(12) United States Patent
Kuroda et al.

(10) Patent No.: US 6,521,649 B1
(45) Date of Patent: Feb. 18, 2003

(54) AGRICULTURAL AND HORTICULTURAL DISEASE CONTROLLER AND A METHOD FOR CONTROLLING THE DISEASES

(75) Inventors: Kiyoshi Kuroda, Sakura (JP); Toru Uchikurohane, Hashimoto (JP); Sokichi Tajima, Osaka (JP); Kenji Tsubata, Kawachinagano (JP)

(73) Assignee: Nihon Nohayku Co., Ltd., Tokyo (JP)

( * ) Notice: Subject to any disclaimer, the term of this patent is extended or adjusted under 35 U.S.C. 154(b) by 115 days.

(21) Appl. No.: 09/666,045

(22) Filed: Sep. 20, 2000

Related U.S. Application Data

(60) Division of application No. 08/941,762, filed on Sep. 30, 1997, now Pat. No. 6,166,054, which is a continuation-in-part of application No. PCT/JP96/00781, filed on Mar. 26, 1996.

(30) Foreign Application Priority Data

Mar. 31, 1995 (JP) .............................. 7-099880

(51) Int. Cl.$^7$ ........................................... A01N 43/828
(52) U.S. Cl. ....................... 514/361; 504/261
(58) Field of Search ........................... 514/361; 504/261

(56) References Cited

U.S. PATENT DOCUMENTS

| 4,177,054 A | 12/1979 | Arndt et al. ................... 71/90 |
| 4,314,839 A | 2/1982 | Kruger et al. .................. 71/73 |
| 4,341,551 A | 7/1982 | Kruger et al. .................. 71/90 |
| 4,358,596 A | * 11/1982 | Kruger ....................... 548/127 |
| 4,956,375 A | * 9/1990 | Oda et al. .................... 514/361 |

FOREIGN PATENT DOCUMENTS

| CA | 2239580 | 6/1997 |
| EP | 0046497 | 3/1982 |
| FR | 2395263 | 1/1979 |
| FR | 2451371 | 10/1980 |
| FR | 2453165 | 10/1980 |
| WO | WO 97/20465 | 6/1997 |
| WO | WO 97/20840 | 6/1997 |

* cited by examiner

*Primary Examiner*—S. Mark Clardy
(74) *Attorney, Agent, or Firm*—Manelli Denison & Seiter PLLC; Paul E. White, Jr.

(57) ABSTRACT

A method for using a compound represented by the general formula:

$$\underset{N}{\overset{N}{\underset{\parallel}{\|}}}\!\!\!-\!\!\!\underset{S}{\overset{R^1}{\underset{C-R^2}{\|}}}\!\!\!\overset{}{\underset{O}{\|}} \quad (I)$$

(wherein $R^1$ and $R^2$ are the substituents, respectively, defined in the specification) for agricultural and horticultural disease control, and a composition used in said method.

10 Claims, No Drawings

AGRICULTURAL AND HORTICULTURAL DISEASE CONTROLLER AND A METHOD FOR CONTROLLING THE DISEASES

This is a division of application Ser. No. 08/941,762 filed Sep. 30, 1997, now U.S. Pat. No. 6,166,054, which is a continuation-in-part of PCT/JP96/00781, filed Mar. 26, 1996.

TECHNICAL FIELD

The present invention relates to an agricultural and horticultural disease controller containing as an active ingredient a 1,2,3-thiadiazole derivative represented by the general formula (1), or a salt thereof:

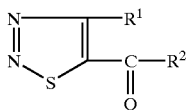

(I)

wherein $R^1$ is ① a hydrogen atom, ② a $(C_1-C_{12})$alkyl group, ③ a halo$(C_1-C_{12})$alkyl group, ④ $(C_2-C_{12})$alkenyl group, ⑤ a halo$(C_2-C_{12})$alkenyl group, ⑥ a $(C_2-C_{12})$ alkynyl group, ⑦ a halo$(C_2-C_{12})$alkynyl group, ⑧ a $(C_3-C_6)$cycloalkyl group, ⑨ an unsubstituted phenyl group, ⑩ a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups, ⑪ a group represented by the formula:

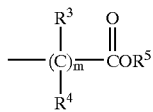

(wherein $R^3$ and $R^4$, which may be the same or different, are hydrogen atoms, $(C_1-C_{12})$alkyl groups or halo$(C_1-C_{12})$ alkyl groups, m is zero or an integer of 1 to 6, and $R^5$ is a hydrogen atom; a $(C_1-C_{12})$alkyl group; a halo$(C_1-C_{12})$alkyl group; a $(C_2-C_{12})$alkenyl group; a $(C_2-C_{12})$alkynyl group; an unsubstituted phenyl group; a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo $(C_1-C_6)$alkylthio groups, $(C_2-C_6)$alkenyl groups and $(C_2-C_6)$alkynyl groups; an unsubstituted phenyl$(C_1-C_6)$ alkyl group; or a substituted phenyl$(C_1-C_6)$alkyl group having on the ring one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$ alkoxy groups, halo$(C_1-C_6)$alkoxy groups, $(C_1-C_6)$ alkylthio groups, halo$(C_1-C_6)$alkylthio groups, $(C_2-C_6)$ alkenyl groups and $(C_2-C_6)$alkynyl groups), ⑫ a group represented by the formula:

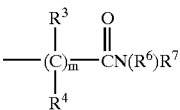

(wherein $R^3$, $R^4$ and m are as defined above, and $R^6$ and $R^7$, which may be the same or different, are hydrogen atoms; $(C_1-C_{12})$alkyl groups; halo$(C_1-C_{12})$alkyl groups; $(C_2-C_{12})$ alkenyl groups; $(C_2-C_{12})$alkynyl groups; $(C_1-C_{12})$alkoxy $(C_1-C_6)$alkyl groups; $(C_1-C_{12})$alkylthio$(C_1-C_6)$alkyl groups; cyano$(C_1-C_{12})$alkyl groups; unsubstituted phenyl groups; substituted phenyl groups having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups; unsubstituted phenyl$(C_1-C_6)$alkyl groups; or substituted phenyl $(C_1-C_6)$alkyl groups having on the ring one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups; $R^6$ and $R^7$ being able to be taken together to represent a $(C_4-C_6)$ alkylene group which may contain an oxygen atom between adjacent carbon atoms of the carbon chain), ⑬ a group represented by the formula:

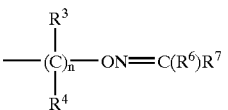

(wherein $R^3$, $R^4$, $R^6$ and $R^7$, and n is an integer of 1 to 6), or ⑭ a group represented by the formula:

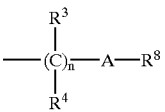

[wherein $R^3$, $R^4$ and n are as defined above, A is

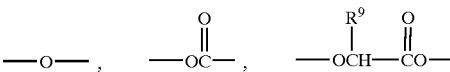

(wherein $R^9$ is a hydrogen atom, a $(C_1-C_{12})$alkyl group or a halo$(C_1-C_{12})$alkyl group),

—S—,

—So—,

—SO$_2$—,

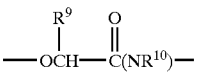

{wherein $R^9$ is as defined above, and $R^{10}$ is a hydrogen atom, a $(C_1-C_{12})$alkyl group or a halo$(C_1-C_{12})$alkyl group, $R^9$ and $R^{10}$ being able to be taken together to represent a $(C_4-C_6)$alkylene group which may contain, between adjacent carbon atoms of the carbon chain, an oxygen atom, a sulfur atom or $$N-R^{11}$$

(wherein $R^{11}$ is a hydrogen atom, a $(C_1-C_{12})$alkyl group or a halo$(C_1-C_{12})$alkyl group)}, or $$-N(R^{10})$$

(wherein $R^{10}$ is as defined above), and $R^8$ is a hydrogen atom; a $(C_1-C_{12})$alkyl group; a halo$(C_1-C_{12})$alkyl group; a $(C_2-C_{12})$alkenyl group; a $(C_2-C_{12})$alkynyl group; a $(C_1-C_{12})$alkoxy$(C_1-C_{12})$alkyl group; a $(C_1-C_{12})$alkylthio$(C_1-C_{12})$alkyl group; a cyano $(C_1-C_{12})$alkyl group; an unsubstituted phenyl group; a substituted phenyl group having one or more substituents which may be the same or different and are selected from the group consisting of halogen atoms, nitro group, cyano group, $(C_1-C_6)$alkyl groups, halo $(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_2-C_6)$alkenyl groups and $(C_2-C_6)$alkynyl groups; an unsubstituted phenyl $(C_1-C_6)$alkyl group; a substituted phenyl$(C_1-C_6)$alkyl group having on the ring one or more substituents which may be the same or different and are selected from the group consisting of halogen atoms, nitro group, cyano group, $(C_1-C_6)$alkyl groups, halo$(C_1-C_6)$ alkyl groups, $(C_1-C_6)$alkoxy groups, halo$(C_1-C_6)$ alkoxy groups, $(C_1-C_6)$alkylthio groups, halo$(C_1-C_6)$ alkylthio groups, $(C_2-C_6)$alkenyl groups and $(C_2-C_6)$ alkynyl groups; an unsubstituted 5- or 6-membered heterocyclic ring having one or more heteroatoms which may be the same or different and are selected from the group consisting of oxygen atom, sulfur atom and nitrogen atom; or a substituted 5- or 6-membered heterocyclic ring having one or more heteroatoms which may be the same or different and are selected from the group consisting of oxygen atom, sulfur atom and nitrogen atom, said substituted heterocyclic ring having one or more substituents which may be the same or different and are selected from the group consisting of halogen atoms, nitro group, cyano group, $(C_1-C_6)$ alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups], and $R^2$ is (i) a group represented by the formula:

$$-X-R^{12}$$

[wherein X is an oxygen atom or a sulfur atom, and $R^{12}$ is ① a hydrogen atom, ② a $(C_1-C_{12})$alkyl group, ③ a halo$(C_1-C_{12})$alkyl group, ④ a $(C_2-C_{12})$alkenyl group, ⑤ a halo$(C_2-C_{12})$alkenyl group, ⑥ a $(C_2-C_{12})$ alkynyl group, ⑦ a halo$(C_2-C_{12})$alkynyl group, ⑧ a hydroxy$(C_1-C_6)$alkyl group, ⑨ a $(C_1-C_{12})$alkoxy $(C_1-C_{12})$alkyl group, ⑩ a $(C_1-C_{12})$alkylthio$(C_1-C_{12})$ alkyl group, ⑪ a $(C_3-C_6)$cycloalkyl group, ⑫ a $(C_3-C_6)$cycloalkyl$(C_1-C_{12})$alkyl group, ⑬ an unsubstituted phenyl group, ⑭ a substituted phenyl group having one or more substituents which may be the same or different and are selected from the group consisting of halogen atoms, nitro group, cyano group, $(C_1-C_6)$ alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups, $(C_2-C_6)$alkynyl groups, and $(C_1-C_6)$ alkoxycarbonyl $(C_1-C_6)$alkyloxy groups, ⑮ an unsubstituted phenyl$(C_1-C_6)$alkyl group, ⑯ a substituted phenyl$(C_1-C_6)$alkyl group having on the ring one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_2-C_6)$alkenyl groups and $(C_2-C_6)$alkynyl groups, ⑰ a diphenyl$(C_1-C_6)$alkyl group, ⑱ a phenoxy$(C_1-C_6)$alkyl group, ⑲ a group represented by the formula:

$$-B-N(R^{13})R^{14}$$

{wherein B is a $(C_1-C_6)$alkylene group which may be substituted by a $(C_1-C_6)$alkyl group or a phenyl group, and $R^{13}$ and $R^{14}$, which may be the same or different, are hydrogen atoms; formyl groups; $(C_1-C_{12})$alkyl groups; $(C_2-C_{12})$alkenyl groups; $(C_2-C_{12})$alkynyl groups; $(C_1-C_6)$alkylcarbonyl groups; unsubstituted phenyl groups; substituted phenyl groups having one or more substituents which may be the same or different and are selected from the group consisting of hydrogen atom, halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups; phenylcarbonyl groups; unsubstituted 1,2,3-thiadiazol-5-yl-carbonyl groups; or substituted 1,2,3-thiadiazol-5-yl-carbonyl groups having a halogen atom or a $(C_1-C_6)$ alkyl group as the substituent; $R^{13}$ and $R^{14}$ being able to be taken together to represent a $(C_4-C_5)$alkylene group which may contain, between adjacent carbon atoms of the carbon chain, an oxygen atom, a sulfur atom or $$N-R^{11}$$

(wherein $R^{11}$ is as defined above)}, ⑳ a group represented by the formula:

$$-C(R^{15})=C(R^{16})-R^{17}$$

(wherein $R^{15}$ is a hydrogen atom or a $(C_1-C_6)$alkyl group, $R^{16}$ is a hydrogen atom, a halogen atom or a $(C_1-C_6)$alkyl group, and $R^{17}$ is a nitro group, a cyano group, a $(C_1-C_6)$alkylcarbonyl group, a $(C_1-C_6)$ alkoxycarbonyl group, a phenylcarbonyl group, or a substituted amino-carbonyl group having one or more substituents which may be the same or different and are selected from the group consisting of hydrogen atom, $(C_1-C_{12})$alkyl groups, unsubstituted phenyl group, and substituted phenyl groups having one or more substituents which may be the same or different and are selected from the group consisting of halogen atoms, cyano group, nitro group, $(C_1-C_6)$alkyl groups and $(C_1-C_6)$alkoxy groups, $R^{15}$ and $R^{17}$ being able to be taken together to represent a $(C_3-C_6)$alkylene group which may be substituted by one or more $(C_1-C_6)$alkyl group and/or an oxo group), ㉑ a group represented by the formula:

$$—CH_2—(CH)_l—CH_2OR^{18}$$
$$|$$
$$O—R^{18}$$

(wherein two $R^{18}$'s, which may be the same or different, are hydrogen atoms, $(C_1-C_6)$alkylcarbonyl groups, phenylcarbonyl groups, unsubstituted 1,2,3-thiadiazol-5-yl-carbonyl groups, or substituted 1,2,3-thiadiazol-5-yl-carbonyl groups having a halogen atom or a $(C_1-C_6)$-alkyl group as the substituent, and l is zero or an integer of 1 to 12), ㉒ a 5- or 6-membered heterocyclic $(C_1-C_6)$alkyl group having one or more heteroatoms which may be the same or different and are selected from the group consisting of oxygen atom, sulfur atom and nitrogen atom, ㉓ tri$(C_1-C_6)$alkylsilyl $(C_1-C_6)$alkyl groups, or ㉔ 1,2,3-thiadiazol-5-yl-carbonyloxy-$(C_1-C_{12})$alkyl groups having on the ring a halogen atom or $(C_1-C_6)$alkyl group as the substituent], (ii) a group represented by the formula:

$$—O—N=C(R^{19})R^{20}$$

[wherein $R^{19}$ and $R^{20}$, which may be the same or different, are ① hydrogen atoms, ② halogen atoms, ③ nitro groups, ④ cyano groups, ⑤ $(C_1-C_{12})$alkyl groups, ⑤ halo$(C_1-C_{12})$alkyl groups, ⑦ $(C_3-C_6)$cycloalkyl groups, ⑧ $(C_2-C_{12})$alkenyl groups, ⑨ $(C_2-C_{12})$alkynyl groups, ⑩ $(C_1-C_{12})$alkoxy$(C_1-C_{12})$alkyl groups, ⑪ $(C_1-C_{12})$alkoxycarbonyl groups, ⑫ unsubstituted phenyl groups, ⑬ substituted phenyl groups having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups, ⑭ unsubstituted 5- or 6-membered heterocyclic rings having one or more heteroatoms which may be the same or different and are selected from the group consisting of oxygen atom, sulfur atom and nitrogen atom, ⑮ substituted 5- or 6-membered hetero-cyclic rings having one or more heteroatoms which may be the same or different and are selected from the group consisting of oxygen atom, sulfur atom and nitrogen atom, said substituted heterocyclic ring having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_2-C_6)$alkenyl groups and $(C_2-C_6)$alkynyl groups, ⑯ groups represented by the formula;

$$—SR^5$$

(wherein $R^5$ is as defined above), or ⑰ groups represented by the formula:

$$—N(R^6)R^7$$

(wherein $R^6$ and $R^7$ are as defined above), $R^{19}$ and $R^{20}$ being able to be taken together to represent ⑱ a $(C_3-C_6)$cycloalkane ring or ⑲ a 5- or 6-membered heterocyclic ring containing, between adjacent carbon atoms of the carbon chain, one or more hetero atoms which may be the same or different and are selected from the group consisting of oxygen atom, sulfur atom and nitrogen atom], (iii) a group represented by the formula:

$$—N(R^{21})R^{22}$$

[wherein $R^{21}$ and $R^{22}$, which may be the same or different, are ① hydrogen atoms, ② $(C_1-C_{12})$alkyl groups, ③ unsubstituted halo$(C_1-C_{12})$alkyl groups, ④ substituted halo$(C_1-C_{12})$alkyl groups having a hydroxyl group or a $(C_1-C_6)$alkoxy group as the substituent, ⑤ $(C_2-C_{12})$alkenyl groups, ⑥ $(C_2-C_{12})$alkynyl groups, ⑦ $(C_1-C_{12})$alkoxy$(C_1-C_6)$alkyl groups, ⑧ $(C_1-C_{12})$alkylthio$(C_1-C_6)$alkyl groups, ⑨ cyano$(C_1-C_{12})$alkyl groups, ⑩ substituted cyano$(C_1-C_6)$alkyl groups having on the alkyl chain a substituent selected from the group consisting of $(C_1-C_6)$alkoxy groups, $(C_2-C_6)$alkenyloxy groups, $(C_2-C_6)$alkynyloxy groups, $(C_1-C_6)$alkylthio groups, $(C_1-C_6)$alkoxycarbonyl$(C_1-C_6)$alkoxy groups, $(C_1-C_6)$alkoxycarbonyl$(C_1-C_6)$alkylthio groups, phenoxy group, phenylthio group and pyrazol-1-yl group, ⑪ unsubstituted carbamoyl$(C_1-C_6)$alkyl groups, ⑫ substituted carbamoyl$(C_1-C_6)$alkyl groups having on the alkyl chain a substituent selected from the group consisting of $(C_1-C_6)$alkoxy groups, $(C_2-C_6)$alkenyloxy groups, $(C_2-C_6)$alkynyloxy groups, $(C_1-C_6)$alkylthio groups, $(C_1-C_6)$alkoxycarbonyl$(C_1-C_6)$alkoxy groups, $(C_1-C_6)$alkoxycarbonyl$(C_1-C_6)$alkylthio groups, phenoxy group, phenylthio group and pyrazol-1-yl group, ⑬ hydroxy-$(C_1-C_6)$alkyl groups, ⑭ di$(C_1-C_6)$alkoxy$(C_1-C_6)$alkyl groups in which the $(C_1-C_6)$alkoxy groups may be the same or different, ⑮ unsubstituted $(C_1-C_6)$alkoxycarbonyl-$(C_1-C_6)$alkyl groups, ⑯ substituted $(C_1-C_6)$alkoxy-carbonyl$(C_1-C_6)$alkyl groups having on the alkyl chain a substituent selected from the group consisting of $(C_1-C_6)$alkyl groups, $(C_1-C_6)$alkoxy groups, $(C_2-C_6)$alkenyloxy groups, $(C_2-C_6)$alkynyloxy groups, $(C_1-C_6)$alkylthio groups, $(C_1-C_6)$alkoxycarbonyl $(C_1-C_6)$alkoxy groups, $(C_1-C_6)$alkoxycarbonyl $(C_1-C_6)$alkylthio groups, phenyl group, phenyl$(C_1-C_6)$alkyl group, phenoxy group, phenylthio group and pyrazol-1-yl group, ⑰ unsubstituted phenyl groups, ⑱ substituted phenyl groups having one or more substituents which may be the same or different and are selected from the group consisting of 1) halogen atoms, 2) nitro group, 3) cyano group, 4) $(C_1-C_6)$alkyl groups, 5) halo$(C_1-C_6)$alkyl groups, 6) $(C_1-C_6)$alkoxy groups, 7) halo$(C_1-C_6)$alkoxy groups, 8) $(C_1-C_6)$alkylthio groups, 9) halo$(C_1-C_6)$alkylthio groups, 10) $(C_2-C_6)$alkenyl groups, 11) $(C_2-C_6)$alkynyl groups, 12) $(C_1-C_6)$alkylcarbonyl groups, 13) carboxyl group, 14) $(C_1-C_{12})$alkoxycarbonyl groups, 15) methylenedioxy group, 16) phenyl group, 17) groups represented by the formula:

$$\overset{O}{\underset{\|}{—C}}—N(R^{23})(R^{24})$$

(wherein $R^{23}$ and $R^{24}$, which may be the same or different, are hydrogen atoms; $(C_1-C_{12})$alkyl groups; halo$(C_1-C_{12})$alkyl groups; $(C_2-C_{12})$alkenyl groups; $(C_2-C_{12})$alkynyl groups; unsubstituted phenyl groups; substituted phenyl groups having one or more substituents which may be the same or different and are selected from the group consisting of halogen atoms, cyano group, nitro group, ($C_1$–$C_6$)alkyl groups and ($C_1$–$C_6$)alkoxy groups; or 5- or 6-membered heterocyclic rings containing, between adjacent carbon atoms of the carbon chain, one or more hetero atoms which may be the same or different and are selected from the group consisting of oxygen atom, sulfur atom and nitrogen atom), 18) groups represented by the formula:

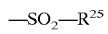

(wherein $R^{25}$ is a hydrogen atom, hydroxyl group, a ($C_1$–$C_{12}$)alkyl group, a halo($C_1$–$C_6$)alkyl group, an unsubstituted phenyl group, a substituted phenyl group having as the substituent(s) one or more substituents which may be the same or different and are selected from the group consisting of halogen atoms, ($C_1$–$C_6$)alkyl groups and ($C_1$–$C_6$)alkoxy groups, unsubstituted 1,2,3-thiadiazol-5-yl group, or substituted 1,2,3-thiadiazol-5-yl groups having halogen atom, ($C_1$–$C_6$)alkyl group or ($C_1$–$C_6$)alkoxy group as the substituent), 19) groups represented by the formula:

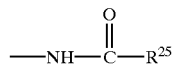

(wherein $R^{25}$ is as defined above), 20) groups represented by the formula:

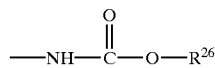

(wherein $R^{26}$ is a ($C_1$–$C_6$)alkyl group, a phenyl group or a phenyl($C_1$–$C_6$)alkyl group), 21) groups represented by the formula:

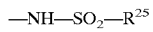

(wherein $R^{25}$ is as defined above), 22) groups represented by the formula:

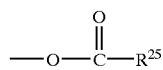

(wherein $R^{25}$ is as defined above), and 23) groups represented by the formula:

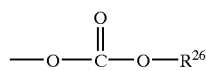

(wherein $R^{26}$ is as defined above), ⑲ unsubstituted phenyl($C_1$–$C_6$)alkyl groups, ⑳ substituted phenyl ($C_1$–$C_6$)alkyl groups having on the ring one or more substituents which may be the same or different and are selected from the group consisting of halogen atoms, nitro group, cyano group, ($C_1$–$C_6$)alkyl groups, halo ($C_1$–$C_6$)alkyl groups, ($C_1$–$C_6$)alkoxy groups, halo ($C_1$–$C_6$)alkoxy groups, ($C_1$–$C_6$)alkylthio groups, halo ($C_1$–$C_6$)alkylthio groups, ($C_2$–$C_6$)alkenyl groups and ($C_2$–$C_6$)alkynyl groups, ㉑ naphthyl groups, ㉒ groups represented by the formula:

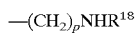

(wherein $R^{18}$ is as defined above, and p is an integer of 1 to 12), or ㉓ 5- or 6-membered heterocyclic rings having one or more hetero atoms which may be the same or different and are selected from the group consisting of oxygen atom, sulfur atom and nitrogen atom, $R^{21}$ and $R^{22}$ being able to be taken together to represent ㉔ a ($C_4$–$C_6$)alkylene group which may contain an oxygen atom between adjacent carbon atoms of the carbon chain, or ㉕ a diaminomethylene group], (iv) a group represented by the formula:

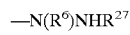

[wherein $R^6$ is as defined above, and $R^{27}$ is ① a hydrogen atom, ② a ($C_1$–$C_{12}$)alkyl group, ③ a halo ($C_1$–$C_{12}$)alkyl group, ④ a ($C_2$–$C_{12}$)alkenyl group, ⑤ a ($C_2$–$C_{12}$)alkynyl group, ⑥ a ($C_1$–$C_{12}$)alkoxy ($C_1$–$C_6$)alkyl group, ⑦ a ($C_1$–$C_{12}$)alkylthio($C_1$–$C_6$) alkyl group, ⑧ a cyano($C_1$–$C_{12}$)alkyl group, ⑨ an unsubstituted phenyl group, ⑩ a substituted phenyl group having one or more substituents which may be the same or different and are selected from the group consisting of halogen atoms, nitro group, cyano group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_2$–$C_6$)alkenyl groups and ($C_2$–$C_6$)alkynyl groups, ⑪ an unsubstituted phenyl($C_1$–$C_6$)alkyl group, ⑫ a substituted phenyl($C_1$–$C_6$)alkyl group having on the ring one or more substituents which may be the same or different and are selected from the group consisting of halogen atoms, nitro group, cyano group, ($C_1$–$C_6$) alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_2$–$C_6$)alkenyl groups and ($C_2$–$C_6$)alkynyl groups, ⑬ a group represented by the formula:

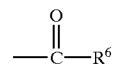

(wherein $R^6$ is as defined above), ⑭ a group represented by the formula:

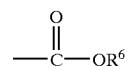

(wherein $R^6$ is as defined above), ⑮ a group represented by the formula:

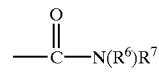

(wherein $R^6$ and $R^7$ are as defined above), or ⑯ a group represented by the formula:

(wherein $R^6$ is as defined above)], (v) a group represented by the formula:

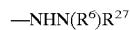

[wherein $R^6$ and $R^{27}$ are as defined above, $R^6$ and $R^{27}$ being able to be taken together to represent

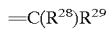

(wherein $R^{28}$ and $R^{29}$, which may be the same or different, are hydrogen atoms; $(C_1-C_6)$alkyl groups; halo$(C_1-C_6)$alkyl groups; $(C_3-C_6)$cycloalkyl groups; unsubstituted phenyl groups; substituted phenyl groups having one or more substituents which may be the same or different and are selected from the group consisting of halogen atoms, $(C_1-C_6)$alkyl groups and $(C_1-C_6)$ alkoxy groups; or 5- or 6-membered heterocyclic rings containing, between adjacent carbon atoms of the carbon chain, one or more hetero atoms which may be the same or different and are selected from the group consisting of oxygen atom, sulfur atom and nitrogen atom; $R^{28}$ and $R^{29}$ being able to be taken together to represent a $(C_3-C_6)$cycloalkane ring or a 5- or 6-membered heterocyclic ring containing one or more sulfur atoms between adjacent carbon atoms of the carbon chain), or $R^6$ and $R^{27}$ being able to be taken together with the nitrogen atom to which they are bonded, to represent a 5- or 6-membered heterocyclic ring which may contain, between adjacent carbon atoms of the carbon chain, one or more hetero atoms which may be the same or different and are selected from the group consisting of oxygen atom, sulfur atom and nitrogen atom], or (vi) a group represented by the formula:

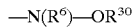

(wherein $R^6$ is as defined above, and $R^{30}$ is a hydrogen atom, a $(C_1-C_{12})$alkyl group, a halo$(C_1-C_{12})$alkyl group, a $(C_3-C_6)$cycloalkyl group, a $(C_1-C_{12})$alkenyl group, a $(C_2-C_{12})$alkynyl group, an unsubstituted phenyl$(C_1-C_6)$alkyl group, or a substituted phenyl $(C_1-C_6)$alkyl group having on the ring one or more substituents which may be the same or different and are selected from the group consisting of halogen atoms, nitro group, cyano group, $(C_1-C_6)$alkyl groups, halo $(C_1-C_6)$alkyl groups, $(C_1-C_6)$alkoxy groups, halo $(C_1-C_6)$alkoxy groups, $(C_2-C_6)$alkenyl groups and $(C_2-C_6)$alkynyl groups).

BACKGROUND ART

Japanese Patent Unexamined Publication No. 54-9272 discloses 1,2,3-thiadiazole-5-carboxylic acid derivatives, a process for production thereof and an agent containing the derivative and having herbicidal and growth-regulating effects.

DISCLOSURE OF THE INVENTION

The present inventors earnestly investigated for developing a novel agricultural and horticultural disease controller and consequently found that 1,2,3-thiadiazole derivatives or salts thereof, which include some of the compounds disclosed in U.S. Pat. No. 4,177,054, are useful for herbicide and growth segulater, whereby the present invention has been accomplished.

BEST MODE FOR CARRYING OUT THE INVENTION

In the definition of the substituents of the 1,2,3-thiadiazole derivative of the general formula (I) used as the active ingredient of the agricultural and horticultural disease controller of the present invention, the halogen atom includes chlorine atom, bromine atom, iodine atom and fluorine atom. The term "$(C_1-C_{12})$alkyl group" means a linear or branched alkyl group of 1 to 12 carbon atoms, such as methyl, ethyl, n-propyl, i-propyl, n-butyl, i-butyl, s-butyl, t-butyl, n-pentyl, n-hexyl, n-heptyl, n-octyl, n-nonyl, n-decyl, n-undecyl, n-dodecyl or the like. The term "halo $(C_1-C_{12})$alkyl group" means a substituted and linear or branched alkyl group of 1 to 12 carbon atoms having as the substituent(s) one or more halogen atoms which may be the same or different. The term "$(C_2-C_6)$alkenyl group" means a linear or branched alkenyl group of 2 to 6 carbon atoms having a double bond. The term "halo-$(C_2-C_6)$alkenyl group" means a substituted and linear or branched alkenyl group of 2 to 6 carbon atoms having as the substituent(s) one or more halogen atoms which may be the same or different. The term "$(C_2-C_6)$alkynyl group" means a linear or branched alkynyl group of 2 to 6 carbon atoms having a triple bond. The term "halo$(C_2-C_6)$alkynyl group" means a substituted and linear or branched alkynyl group of 2 to 6 carbon atoms having as the substituent(s) one or more halogen atoms which may be the same or different.

The term "5- or 6-membered heterocyclic ring having one or more heteroatoms which may be the same or different and are selected from the group consisting of oxygen atom, sulfur atom and nitrogen atom" means any heterocyclic ring derived from furan, thiophene, pyrrole, oxazole, thiazole, isothiazole, pyrazole, imidazole, 1,2,3-thiadiazole, 1,2,4-thiadiazole, 1,2,5-thiadiazole, 1,3,4-thiadiazole, 1,2,4-triazole, pyridine, pyridazine, pyrimidine, pyrazine, pynolidine, piperidine, morpholine, thiamorpholine, dithiolane, dithian, piperazine, dioxelan, imidazolizine and the like.

Preferable examples of the substituents of the 1,2,3-thiadiazole derivative of the general formula (I) used in the present invention are as follows. There is preferably used a compound in which $R^1$ is a $(C_1-C_{12})$alkyl group, halo $(C_1-C_{12})$alkyl group, $(C_3-C_6)$cycloalkyl group, $(C_2-C_{12})$ alkenyl group, halo$(C_2-C_{12})$alkenyl group, $(C_2-C_{12})$alkynyl group, halo$(C_2-C_{12})$alkynyl group, unsubstituted phenyl group or substituted phenyl group, and $R^2$ is —X—$R^{12}$. There is more preferably used a compound in which $R^1$ is a $(C_1-C_6)$alkyl group such as methyl, ethyl, n-propyl, i-propyl, n-butyl, i-butyl, s-butyl, t-butyl, n-pentyl or n-hexyl, and $R^2$ is a hydroxyl group, its salt, a thiol group, its salt, an amide group, or an anilide group.

There is most preferably used a compound in which $R^1$ is a methyl group and $R^2$ is a hydroxyl group, its salt, a thiol group, its salt, an amide group, or an anilide group.

As the salt of the 1,2,3-thiadiazole derivative of the general formula (I), there can be exemplified salts with alkali metals such as sodium, potassium, etc.; salts with alkaline earth metals such as calcium, magnesium, etc.; unsubstituted ammonium salt; substituted ammonium salts having one or more substituents which may be the same or different and are selected from the group consisting of $(C_1-C_{12})$alkyl groups, unsubstituted phenyl group, substituted phenyl groups, unsubstituted benzyl group and substituted benzyl groups; and guanidium salt.

The 1,2,3-thiadiazole derivative of the general formula (I) or salt thereof used as the active ingredient of the agricultural and horticultural disease controller of the present invention can be produced, for example, by any of the processes exemplified below:

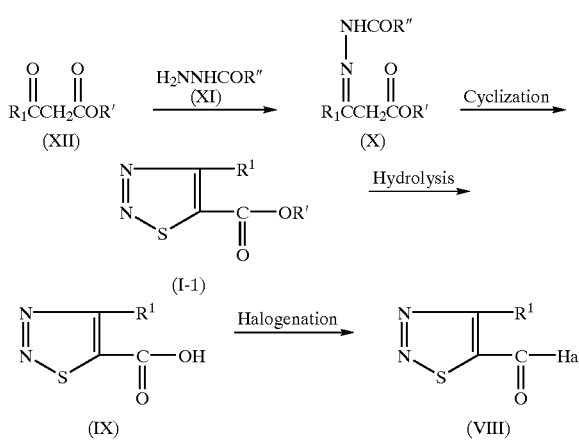

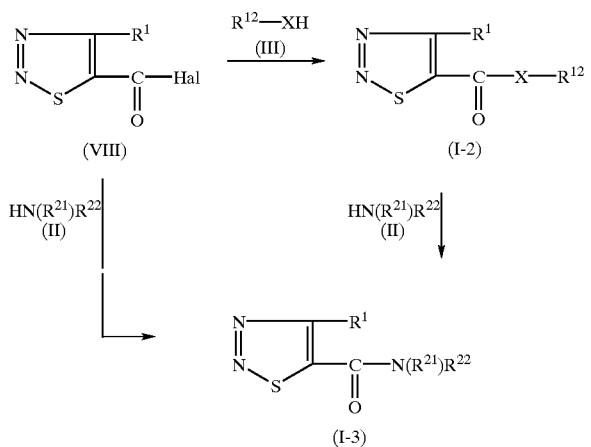

wherein $R^1$ is as defined above, $R^1$ is a $(C_1-C_6)$alkyl group, R″ is an amino group or a $(C_1-C_6)$alkyl group, and Hal is a halogen atom.

A compound of the general formula (XII) is reacted with a compound of the general formula (XI) to obtain a compound of the general formula (X). The compound (X) is cyclized after or without isolation to obtain a 1,2,3-thiadiazole derivative of the general formula (I-1). The derivative (I-1) is hydrolyzed after or without isolation to obtain a compound of the general formula (IX). The compound (IX) is halogenated after or without isolation, whereby the acid halide of the general formula (VIII) can be produced.

The compound of the general formula (XII) can be produced by the process described in J. Org. Chem., 43, 2087 (1978), Formation of C—C bonds, Vol. 3, p. 259, 1979 (Georg Thime Publishers, Stuttgart), etc.

From the acid halide of the general formula (VIII) produced by the above process, the 1,2,3-thiadiazole derivative of the general formula (I) or salt thereof used as the active ingredient of the agricultural and horticultural disease controller of the present invention can be produced, for example, by any of the processes illustrated below.

Production Process 1 wherein $R^1$, $R^{12}$, $R^{21}$, $R^{22}$ and Hal are as defined above.

The acid halide of the general formula (VIII) is reacted with an alcohol of the general formula (III) to obtain a 1,2,3-thiadiazole derivative of the general formula (I-2). The compound (I-2) is reacted with an amine of the general formula (II) after or without isolation of the compound (I-2), whereby a 1,2,3-thiadiazole derivative of the general formula (1I-3) can be produced.

The 1,2,3-thiadiazole derivative of the general formula (I-3) can be produced also by reacting the acid halide of the general formula (VIII) with an amine of the general formula (II).

Production Process 2

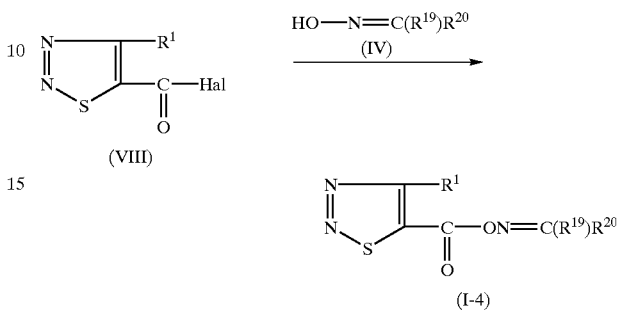

wherein $R^{19}$, $R^{20}$ and Hal are as defined above.

A 1,2,3-thiadiazole derivative of the general formula (I-4) can be produced by reacting the acid halide of the general formula (VIII) with a compound of the general formula (IV).

Production Process 3

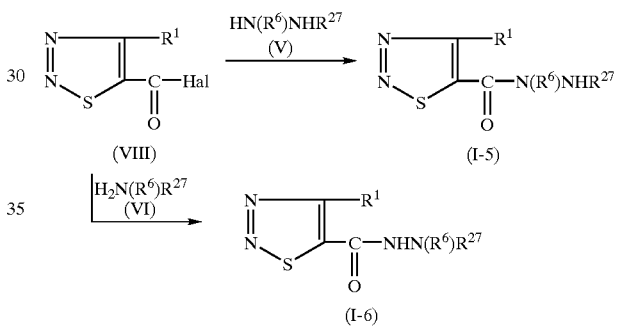

wherein $R^6$, $R^{27}$ and Hal are as defined above.

A 1,2,3-thiadiazole derivative of the general formula (I-5) can be produced by reacting the acid halide of the general formula (VIII) with a compound of the general formula (V). Similarly, a 1,2,3-thiadiazole derivative of the general formula (I-6) can be produced by reacting the acid halide of the general formula (VIII) with a compound of the general formula (VI).

Production Process 4

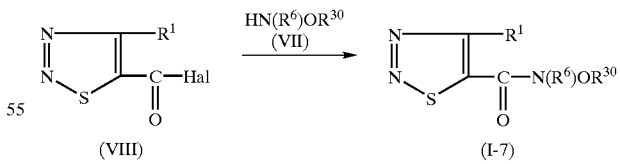

wherein $R^6$, $R^{30}$ and Hal are as defined above.

A 1,2,3-thiadiazole derivative of the general formula (I-7) can be produced by reacting the acid halide of the general formula (VIII) with a compound of the general formula (VII).

Typical compounds as the 1,2,3-thiadiazole derivative of the general formula (I) or a salt thereof are listed in Table 1 but they are not intended in any way to limit the scope of the present invention.

The abbreviations in the R¹ column and R² column in Table 1 stand for the following compounds:
TABLE 1
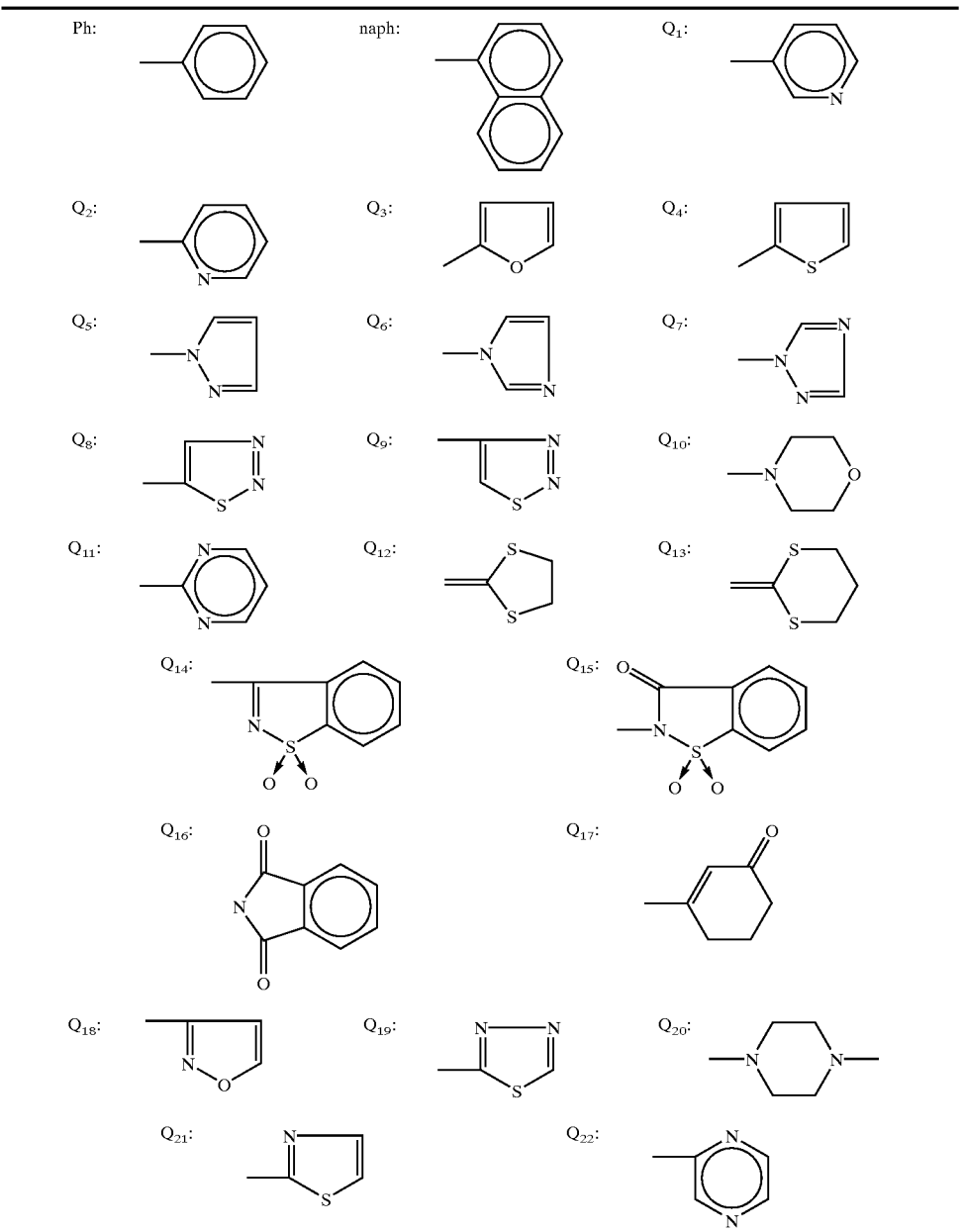
General formula (I)
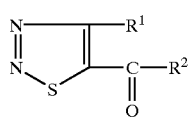
(I)
| No | R¹ | R² | Physical property |
|----|----|----|-------------------|
| 1 | H | OH | m.p. 107.1° C. |
| 2 | H | OC$_2$H$_5$ | nD 1.5060 (20.1° C.) |
| 3 | H | NH$_2$ | m.p. 160.8° C. |
| 4 | H | NH—Ph | m.p. 132.0° C. |
| 5 | H | NH—CH(Q$_5$)—CN | m.p. 163.9° C. |
| 6 | H | NHOCH$_3$ | m.p. 113.1° C. |

TABLE 1-continued

| | | | |
|---|---|---|---|
| 7 | $CH_3$ | OH | m.p. 188–189.5° C. |
| 8 | $CH_3$ | O—Na | m.p. 230° C. (decomp.) |
| 9 | $CH_3$ | O—K | m.p. 243° C. (decomp.) |
| 10 | $CH_3$ | O—Li | m.p. 280° C. (decomp.) |
| 11 | $CH_3$ | O—Ag | m.p. 190° C. (decomp.) |
| 12 | $CH_3$ | O—½Ca | m.p. 250° C. (decomp.) |
| 13 | $CH_3$ | O—$NH_4$ | m.p. 130° C. (decomp.) |
| 14 | $CH_3$ | O—$NH_2C(NH_2)=NH_2$ | m.p. 146° C. |
| 15 | $CH_3$ | $OCH_3$ | nD 1.5165 (23.2° C.) |
| 16 | $CH_3$ | $OC_2H_5$ | nD 1.5075 (14.0° C.) |
| 17 | $CH_3$ | $OC_3H_7$-n | nD 1.4000 (12.5° C.) |
| 18 | $CH_3$ | $OC_3H_7$-i | nD 1.4400 (14.3° C.) |
| 19 | $CH_3$ | $OC_4H_9$-s | nD 1.4165 (24.2° C.) |
| 20 | $CH_3$ | $OC_4H_9$-t | nD 1.4245 (16.9° C.) |
| 21 | $CH_3$ | $OCH(CH_2CH_3)_2$ | nD 1.3211 (24.5° C.) |
| 22 | $CH_3$ | $OC_8H_{17}$-n | nD 1.4900 (12.9° C.) |
| 23 | $CH_3$ | $OC_{11}H_{23}$-n | nD 1.4946 (18.4° C.) |
| 24 | $CH_3$ | $OC_{15}H_{31}$-n | NMR |
| 25 | $CH_3$ | $OCH_2CH_2Br + OCH_2CH_2I = 2:1$ | nD 1.5615 (20.7° C.) |
| 26 | $CH_3$ | $OCH_2CH=CH_2$ | nD 1.5153 (15.0° C.) |
| 27 | $CH_3$ | $O(CH_2)_8CH=CHCH_2CH=(CH_2)_4CH_3$<br>cis    cis | nD 1.502 (26.3° C.) |
| 28 | $CH_3$ | O—$CH_2C\equiv CH$ | nD 1.3405 (13.8° C.) |
| 29 | $CH_3$ | O-cyclo-$C_6H_{11}$ | nD 1.5248 (25.2° C.) |
| 30 | $CH_3$ | O—$CH_2$-cyclo-$C_3H_5$ | nD 1.5241 (26.5° C.) |
| 31 | $CH_3$ | O—$CH_2COOC_2H_5$ | nD 1.5074 (25.5° C.) |
| 32 | $CH_3$ | O—$CH_2COCH_3$ | m.p. 55.7–56.8° C. |
| 33 | $CH_3$ | O—Ph | nD 1.5845 (20.6° C.) |
| 34 | $CH_3$ | O-(4-Cl—Ph) | m.p. 77–80° C. |
| 35 | $CH_3$ | O-(2-$CH_3$—Ph) | m.p. 62–64° C. |
| 36 | $CH_3$ | O-(3-$CH_3$—Ph) | m.p. 51–53° C. |
| 37 | $CH_3$ | O-(4-$CH_3$—Ph) | m.p. 31° C. |
| 38 | $CH_3$ | O-(4-$OCH_3$—Ph) | m.p. 73° C. |
| 39 | $CH_3$ | O-(4-$OCH(CH_3)COOC_2H_5$—Ph) | nD 1.5433 (26.5° C.) |
| 40 | $CH_3$ | O—$CH_2$—Ph | nD 1.5735 (13.1° C.) |
| 41 | $CH_3$ | O—$CH_2$-(4-Cl—Ph) | m.p. 85° C. |
| 42 | $CH_3$ | O—$CH_2$-(4-$NO_2$—Ph) | m.p. 100° C. |
| 43 | $CH_3$ | O—$CH_2$-(4-$CH_3$—Ph) | m.p. 52° C. |
| 44 | $CH_3$ | O—$CH_2$(4-t-$C_4H_9$—Ph) | nD 1.5558 (26.3° C.) |
| 45 | $CH_3$ | O—$CH_2$(3-O—Ph—Ph) | nD 1.6029 (26.4° C.) |
| 46 | $CH_3$ | O—$CH_2$(2,4-$Cl_2$—Ph) | m.p. 74° C. |
| 47 | $CH_3$ | O—$CH_2$(2,6-$Cl_2$—Ph) | m.p. 97° C. |
| 48 | $CH_3$ | O—$CH_2$(3,5-$Cl_2$—Ph) | m.p. 81° C. |
| 49 | $CH_3$ | O—$CH_2$(2-$OCH_3$—Ph) | m.p. 60° C. |
| 50 | $CH_3$ | O—$CH(Ph)_2$ | nD 1.6030 (26.4° C.) |
| 51 | $CH_3$ | O—$CH_2$-(4-$OCH_3$—Ph) | nD 1.5774 (26.2° C.) |
| 52 | $CH_3$ | O—$CH_2$—($F_5$—Ph) | m.p. 61° C. |
| 53 | $CH_3$ | O—$CH_2CH_2O$—Ph | m.p. 78° C. |
| 54 | $CH_3$ | O—$CH(CH_3)$—Ph | nD 1.5631 (25.0° C.) |
| 55 | $CH_3$ | O—$CH_2CH_2Si(CH_3)_3$ | nD 1.501 (20.2° C.) |
| 56 | $CH_3$ | O—$CH_2$—$Q_1$ | nD 1.5730 (28.0° C.) |
| 57 | $CH_3$ | O—$CH_2$-(4-$CH_3$—$Q_8$) | nD 1.5842 (25.0° C.) |
| 58 | $CH_3$ | O—$CH_2CH_2O$—$Q_{14}$ | m.p. 137° C. |
| 59 | $CH_3$ | O—$CH_2CH_2$—$Q_{15}$ | m.p. 102° C. |
| 60 | $CH_3$ | O—$CH_2CH_2O$—$Q_{10}$ | nD 1.5280 (28.0° C.) |
| 61 | $CH_3$ | O—$CH_2$—$Q_7$ | m.p. 68–74° C. |
| 62 | $CH_3$ | O—$Q_{17}$ | nD 1.5678 (28.8° C.) |
| 63 | $CH_3$ | O-5,5-$(CH_3)_2$—$Q_{17}$) | nD 1.5498 (28.7° C.) |
| 64 | $CH_3$ | O—$CH_2CH_2O$—CO-(4-$CH_3$—$Q_8$) | NMR |
| 65 | $CH_3$ | O—$N=C_6H_{10}$-cyclo | nD 1.461 (13.5° C.) |
| 66 | $CH_3$ | O—$N=C(CH_3)_2$ | nD 1.5422 (19.8° C.) |
| 67 | $CH_3$ | O—$N=CH$—Ph | m.p. 113.5° C. |
| 68 | $CH_3$ | O—$N=C(CH_3)$—Ph | m.p. 99.9° C. |
| 69 | $CH_3$ | O—$Q_{16}$ | m.p. >185° C. (sublimation) |
| 70 | $CH_3$ | O—$N=Q_{12}$ | m.p. 114.5° C. |
| 71 | $CH_3$ | O—$N=Q_{13}$ | m.p. 100.1° C. |
| 72 | $CH_3$ | $SCH_3$ | m.p. 40.1° C. |
| 73 | $CH_3$ | $SC_2H_5$ | nD 1.5229 (20.8° C.) |
| 74 | $CH_3$ | $SC_3H_7$-n | nD 1.4499 (20.9° C.) |
| 75 | $CH_3$ | $SC_3H_7$-i | nD 1.5620 (21.8° C.) |
| 76 | $CH_3$ | $SC_4H_9$-i | nD 1.4546 (21.6° C.) |
| 77 | $CH_3$ | $SC_4H_9$-t | nD 1.5743 (21.0° C.) |
| 78 | $CH_3$ | $SC_8H_{17}$-n | nD 1.5361 (25.4° C.) |
| 79 | $CH_3$ | $SC_{12}H_{25}$-n | nD 1.5261 (18.6° C.) |
| 80 | $CH_3$ | S-cyclo-$C_6H_{11}$ | nD 1.5743 (20.8° C.) |
| 81 | $CH_3$ | S-(4-$CH_3$—Ph) | nD 1.6261 (21.2° C.) |
| 82 | $CH_3$ | S—$CH_2$—Ph | nD 1.6239 (21.1° C.) |
| 83 | $CH_3$ | S—$CH_2$-(4-Cl—Ph) | m.p. 74.5° C. |
| 84 | $CH_3$ | $NH_2$ | m.p. 115° C. |

TABLE 1-continued

| | | | |
|---|---|---|---|
| 85 | $CH_3$ | $NHCH_3$ | m.p. 45° C. |
| 86 | $CH_3$ | $N(CH_3)_2$ | nD 1.5555 (13.2° C.) |
| 87 | $CH_3$ | $NHC_2H_5$ | m.p. 44° C. |
| 88 | $CH_3$ | $N(C_2H_5)_2$ | nD 1.5365 (13.7° C.) |
| 89 | $CH_3$ | $NHC_3H_7$-i | m.p. 65° C. |
| 90 | $CH_3$ | $NHC_4H_9$-n | |
| 91 | $CH_3$ | $NHC_6H_{11}$-cyclo | m.p. 98° C. |
| 92 | $CH_3$ | $NHCH_2CH_2OCH_3$ | nD 1.5359 (26.0° C.) |
| 93 | $CH_3$ | $NHCH_2CH_2CH_2OCH_3$ | nD 1.5273 (26.0° C.) |
| 94 | $CH_3$ | $NHCH_2CH(OCH_3)_2$ | nD 1.5240 (26.1° C.) |
| 95 | $CH_3$ | $N(CH_2CH=CH_2)_2$ | nD 1.5535 (27.5° C.) |
| 96 | $CH_3$ | $NHC(CH_3)_2$—C≡CH | NMR |
| 97 | $CH_3$ | $NHCH(CH_3)CH_2OH$ | NMR |
| 98 | $CH_3$ | $NHCH_2CN$ | m.p. 76–78° C. |
| 99 | $CH_3$ | $NHCH_2CH_2CN$ | m.p. 86–87° C. |
| 100 | $CH_3$ | $N(CH_2CH_2CN)_2$ | m.p. 110–115° C. |
| 101 | $CH_3$ | $NHC(CH_3)(i-C_3H_7)$—CN | nD 1.5235 (25.9° C.) |
| 102 | $CH_3$ | $NHCH(C_3H_7$-i$)COOCH_3$ | NMR |
| 103 | $CH_3$ | $NHCH(CH_3)CH_2COOC_2H_5$ | nD 1.5250 (20.4° C.) |
| 104 | $CH_3$ | NHPh | m.p. 110° C. |
| 105 | $CH_3$ | NH(2-Cl—Ph) | m.p. 101° C. |
| 106 | $CH_3$ | NH(3-Cl—Ph) | m.p. 136–142° C. |
| 107 | $CH_3$ | NH(4-Cl—Ph) | m.p. 114° C. |
| 108 | $CH_3$ | NH(2-F—Ph) | m.p. 120° C. |
| 109 | $CH_3$ | NH(3-F—Ph) | m.p. 127° C. |
| 110 | $CH_3$ | NH(4-F—Ph) | m.p. 103° C. |
| 111 | $CH_3$ | NH(2-$CH_3$—Ph) | m.p. 115° C. |
| 112 | $CH_3$ | NH(3-$CH_3$—Ph) | m.p. 111° C. |
| 113 | $CH_3$ | NH(4-$CH_3$—Ph) | m.p. 109° C. |
| 114 | $CH_3$ | NH(3-i-$C_3H_7$—Ph) | NMR |
| 115 | $CH_3$ | NH(2-$OCH_3$—Ph) | m.p. 112° C. |
| 116 | $CH_3$ | NH(3-$OCH_3$—Ph) | m.p. 107–110° C. |
| 117 | $CH_3$ | NH(4-$OCH_3$—Ph) | m.p. 117° C. |
| 118 | $CH_3$ | NH(3-O-i-$C_3H_7$—Ph) | NMR |
| 119 | $CH_3$ | NH(4-$NO_2$—Ph) | m.p. 175° C. |
| 120 | $CH_3$ | NH(3-CN—Ph) | m.p. 161° C. |
| 121 | $CH_3$ | NH(4-CN—Ph) | m.p. 172° C. |
| 122 | $CH_3$ | NH(4-$CO_2H$—Ph) | m.p. 257° C. (decomp.) |
| 123 | $CH_3$ | NH(4-$CO_2CH_3$—Ph) | m.p. 133° C. |
| 124 | $CH_3$ | NH(4-$CO_2C_2H_5$—Ph) | m.p. 118° C. |
| 125 | $CH_3$ | NH(3-$COCH_3$—Ph) | m.p. 154° C. |
| 126 | $CH_3$ | NH(4-$COCH_3$—Ph) | m.p. 128° C. |
| 127 | $CH_3$ | NH(2-Ph—Ph) | m.p. 85.5° C. |
| 128 | $CH_3$ | NH(2,4-$Cl_2$—Ph) | m.p. 118–119° C. |
| 129 | $CH_3$ | NH(2,5-$Cl_2$—Ph) | m.p. 151–155° C. |
| 130 | $CH_3$ | NH(3,4-$Cl_2$—Ph) | m.p. 138–139° C. |
| 131 | $CH_3$ | NH(3,5-$Cl_2$—Ph) | m.p. 197–199° C. |
| 132 | $CH_3$ | NH(2,4-$(CH_3)_2$—Ph) | m.p. 98.3–98.9° C. |
| 133 | $CH_3$ | NH(2,6-$(CH_3)_2$—Ph) | m.p. 95–99° C. |
| 134 | $CH_3$ | NH(3,5-$(CF_3)_2$—Ph) | m.p. 170° C. |
| 135 | $CH_3$ | NH(3-$OCH_2$O-4-Ph) | m.p. 138° C. |
| 136 | $CH_3$ | NH(2,4,6-$(CH_3)_3$—Ph) | m.p. 115–117° C. |
| 137 | $CH_3$ | NH(2,6-$Br_2$-4-$OCF_3$—Ph) | m.p. 151.7° C. |
| 138 | $CH_3$ | NH($F_5$—Ph) | m.p. 124° C. |
| 139 | $CH_3$ | NH—$CH_2$—Ph | m.p. 53° C. |
| 140 | $CH_3$ | $N(CH_3)$—Ph | paste NMR |
| 141 | $CH_3$ | $NHC(CH_3)_2$—Ph | m.p. 139° C. |
| 142 | $CH_3$ | $NHCH_2$-(4-Cl—Ph) | m.p. 102–105° C. |
| 143 | $CH_3$ | $NHCH(CH_3)$(4-Cl—Ph) | m.p. 108° C. |
| 144 | $CH_3$ | $NHCH(CH_2$—Ph$)COOCH_3$ | NMR |
| 145 | $CH_3$ | NH-naph | m.p. 151° C. |
| 146 | $CH_3$ | NH—$Q_2$ | m.p. 130° C. |
| 147 | $CH_3$ | $Q_{10}$ | m.p. 92° C. |
| 148 | $CH_3$ | 2,6-$(CH_3)_2$—$Q_{10}$ (cis) | m.p. 96–100° C. |
| 149 | $CH_3$ | $NHCH_2$—$Q_3$ | nD 1.5731 (26.1° C.) |
| 150 | $CH_3$ | $NHCH(OC_2H_5)$—CN | paste NMR |
| 151 | $CH_3$ | $NHCH(OCH_2C≡CH)$—CN | NMR |
| 152 | $CH_3$ | $NHCH(Q_5)$—CN | m.p. 157.3° C. |
| 153 | $CH_3$ | $NHCH(3,5-(CH_3)_2$—$Q_5)$—CN | m.p. 155.6° C. |
| 154 | $CH_3$ | $NHCH(SCH(CH_3)$—$C_2H_5)$—CN | paste NMR |
| 155 | $CH_3$ | $NHCH(S$—Ph$)$—CN | m.p. 116.5° C. |
| 156 | $CH_3$ | $NHSO_2$—Ph | m.p. 170–176° C. |
| 157 | $CH_3$ | $N=C(NH_2)_2$ | m.p. 245° C. |
| 158 | $CH_3$ | $NHNH_2$ | m.p. 143.8° C. |
| 159 | $CH_3$ | $N(CH_3)NH_2$ + $NHNHCH_3$ = 4:1 | m.p. 96.7–104.0° C. |
| 160 | $CH_3$ | $NHN(CH_3)_2$ | m.p. 149–154° C. |
| 161 | $CH_3$ | NHNHCO—Ph | m.p. 183.4° C. |
| 162 | $CH_3$ | NH—$Q_{10}$ | m.p. 191.0° C. |

TABLE 1-continued

| | | | |
|---|---|---|---|
| 163 | $CH_3$ | $NHN=C(CH_3)_2$ | m.p. 198° C. |
| 164 | $CH_3$ | $NHN=C(CH_3)C_2H_5$ | m.p. 152–153° C. |
| 165 | $CH_3$ | $NHN=CH-Ph$ | m.p. 238° C. |
| 166 | $CH_3$ | $NHN=C(cyclo-C_3H_5)Ph$ | m.p. 156° C. (Mixture of E- and Z-forms) |
| 167 | $CH_3$ | $NHN=C(CH_3)Ph$ | m.p. 260–270° C. |
| 168 | $CH_3$ | $NHN=C(CH_3)(2-CH_3-Ph)$ | m.p. 146.6° C. (upper spot in TLC) |
| 169 | $CH_3$ | $NHN=C(CH_3)(2-CH_3-Ph)$ | m.p. 153.0° C. Lower spot in TLC |
| 170 | $CH_3$ | $NHN=C(CH_3)Q_3$ | m.p. 286–288° C. |
| 171 | $CH_3$ | $NHN=C(CH_3)Q_2$ | m.p. 215–216° C. |
| 172 | $CH_3$ | $NHN=Q_{12}$ | m.p. 239.7° C. |
| 173 | $CH_3$ | $NHOCH_3$ | m.p. 70° C. |
| 174 | $CH_3$ | $NHOCH_2-Ph$ | m.p. 73° C. |
| 175 | $C_2H_5$ | OH | m.p. 137.1–138.4° C. |
| 176 | $C_2H_5$ | ONa | m.p. 250° C. (decomp.) |
| 177 | $C_2H_5$ | $O-PhCH_2N(CH_3)_3$ | m.p. 115–117° C. |
| 178 | $C_2H_5$ | $O-NH_3C_4H_9$-t | m.p. 105–107° C. |
| 179 | $C_2H_5$ | O-½pyridinium | m.p. 62–63° C. |
| 180 | $C_2H_5$ | $OCH_3$ | nD 1.5093 (24.1° C.) |
| 181 | $C_2H_5$ | $OCH_2-Ph$ | nD 1.5539 (23.7° C.) |
| 182 | $C_2H_5$ | $NH_2$ | m.p. 139.0° C. |
| 183 | $C_2H_5$ | $NH-Ph$ | m.p. 81.9° C. |
| 184 | n-$C_3H_7$ | $OC_2H_5$ | nD 1.4958 (21.0° C.) |
| 185 | i-$C_3H_7$ | OH | m.p. 136.6° C. |
| 186 | i-$C_3H_7$ | O-Na | NMR |
| 187 | i-$C_3H_7$ | $O-NH_4$ | m.p. 169.9° C. |
| 188 | i-$C_3H_7$ | $OC_2H_5$ | nD 1.4934 (20.9° C.) |
| 189 | i-$C_3H_7$ | $OC_8H_{17}$-n | nD 1.4845 (21.8° C.) |
| 190 | i-$C_3H_7$ | $OCH_2-Ph$ | nD 1.5505 (23.8° C.) |
| 191 | i-$C_3H_7$ | $NH_2$ | m.p. 137.3° C. |
| 192 | i-$C_3H_7$ | $NH-Ph$ | m.p. 112.3° C. |
| 193 | i-$C_3H_7$ | $NH-CH_2-CN$ | paste NMR |
| 194 | i-$C_3H_7$ | $NH-CH(Q_5)-CN$ | m.p. 107.4° C. |
| 195 | n-$C_4H_9$ | OH | m.p. 92.3° C. |
| 196 | n-$C_4H_9$ | O-Na | m.p. 188.5° C. |
| 197 | n-$C_4H_9$ | $OCH_3$ | nD 1.4993 (22.3° C.) |
| 198 | t-$C_4H_9$ | OH | m.p. 111.1° C. |
| 199 | t-$C_4H_9$ | $OCH_3$ | nD 1.5082 (13.0° C.) |
| 200 | n-$C_5H_{11}$ | OH | m.p. 86.2° C. |
| 201 | n-$C_5H_{11}$ | $OCH_3$ | nD 1.4969 (22.5° C.) |
| 202 | $CH_2Cl$ | OH | m.p. 120.9° C. |
| 203 | $CH_2Cl$ | O-Na | m.p. 280° C. (decomp.) |
| 204 | $CH_2Cl$ | $OCH_3$ | nD 1.5315 (19.2° C.) |
| 205 | $CH_2Br$ | OH | m.p. 117.4° C. |
| 206 | $CH_2Br$ | $OCH_3$ | nD 1.5743 (13.1° C.) |
| 207 | $CF_3$ | OH | nD 1.4590 (23.7° C.) |
| 208 | $CF_3$ | $OCH_3$ | nD 1.4513 (23.6° C.) |
| 209 | $CF_3$ | $OC_2H_5$ | nD 1.4451 (23.6° C.) |
| 210 | $CF_3$ | $NH_2$ | m.p. 143.7° C. |
| 211 | $CF_3$ | $NH-Ph$ | m.p. 142.7° C. |
| 212 | $CF_3$ | $NH(3$-i-$C_3H_7-Ph)$ | m.p. 81.3° C. |
| 213 | $CF_3$ | $NH(3$-i-$C_3H_7O-Ph)$ | paste NMR |
| 214 | $CF_3$ | $NH$-$(3,5$-$(CF_3)_2$-$Ph)$ | m.p. 156.2° C. |
| 215 | $CF_3$ | $NH-CH(Q_5)-CN$ | m.p. 118.9° C. |
| 216 | $CF_3$ | $NHOCH_3$ | m.p. 101.9° C. |
| 217 | $CHBrCH_3$ | OH | m.p. 114.8° C. |
| 218 | $CHBrCH_3$ | $OCH_3$ | nD 1.5545 (22.7° C.) |
| 219 | $CH_2CH_2CH_2Cl$ | $OCH_3$ | nD 1.5271 (24.0° C.) |
| 220 | cyclo-$C_3H_5$ | OH | m.p. 157.1° C. |
| 221 | cyclo-$C_3H_5$ | $OCH_3$ | m.p. 47.4° C. |
| 222 | cyclo-$C_3H_5$ | $OC_2H_5$ | nD 1.5304 (22.1° C.) |
| 223 | cyclo-$C_3H_5$ | $OCH_2-Ph$ | nD 1.5815 (22.1° C.) |
| 224 | cyclo-$C_3H_5$ | $ON=Q_{12}$ | m.p. 160.6° C. |
| 225 | cyclo-$C_3H_5$ | $NH_2$ | m.p. 162.7° C. |
| 226 | cyclo-$C_3H_5$ | $NH-Ph$ | m.p. 138.8° C. |
| 227 | cyclo-$C_3H_5$ | $NH$-$(3$-i-$C_3H_7-Ph)$ | paste NMR |
| 228 | cyclo-$C_3H_5$ | $NH(3$-i-$C_3H_7O-Ph)$ | paste NMR |
| 229 | $CH_2OCH_3$ | OH | m.p. 104.8° C. |
| 230 | $CH_2OCH_3$ | $OCH_3$ | m.p. 40.4° C. |
| 231 | $CH_2O-COCH_3$ | $OCH_3$ | nD 1.5122 (19.1° C.) |
| 232 | $CH_2S-Ph$ | OH | m.p. 133.6° C. |
| 233 | $CH_2S-Ph$ | $OCH_3$ | nD 1.6210 (19.5° C.) |
| 234 | $CH_2S$-$(4$-$Cl$-$Ph)$ | OH | m.p. 143.8° C. |
| 235 | $CH_2S$-$(4$-$Cl$-$Ph)$ | $OCH_3$ | nD 1.6268 (19.6° C.) |
| 236 | COOH | $NHC(CH_3)(i$-$C_3H_7)-CN$ | nD 1.4832 (25.1° C.) |
| 237 | $COOC_2H_5$ | OH | m.p. 68.9° C. |
| 238 | $COOC_2H_5$ | $OC_2H_5$ | nD 1.5008 (21.4° C.) |

TABLE 1-continued

| | | | |
|---|---|---|---|
| 239 | COOC$_2$H$_5$ | OC$_4$H$_9$-n | |
| 240 | COOC$_2$H$_5$ | NH—Ph | m.p. 125.4° C. |
| 241 | COOC$_4$H$_9$-n | O—C$_4$H$_9$-n | nD 1.4928 (24.2° C.) |
| 242 | COOC$_4$H$_9$-n | NHCH$_2$—Ph | paste NMR |
| 243 | CONHCH$_3$ | NHCH$_3$ | m.p. 195–196° C. |
| 244 | CONHC$_3$H$_7$-i | NHC$_3$H$_7$-I | m.p. 92–96° C. |
| 245 | CONHCH$_2$CH$_2$OCH$_3$ | NHCH$_2$CH$_2$OCH$_3$ | m.p. 90–92° C. |
| 246 | CONHCH$_2$Ph | OC$_4$H$_9$-n | paste NMR |
| 247 | CONHCH$_2$Ph | NHCH$_2$Ph | m.p. 113.8–116.3° C. |
| 248 | CON(CH$_3$)CH$_2$Ph | OC$_2$H$_5$ | |
| 249 | CH$_2$COOH | OH | m.p. 159–160° C. (decomp.) |
| 250 | CH$_2$COOCH$_3$ | OCH$_3$ | nD 1.5165 (21.4° C.) |
| 251 | CH$_2$COOCH$_3$ | OC$_4$H$_9$-n | nD 1.4956 (23.9° C.) |
| 252 | CH$_2$CONHC$_3$H$_7$-i | NHC$_3$H$_7$-i | m.p. 146–156° C. |
| 253 | CH$_2$CONHC$_5$H$_{11}$-i | NHC$_5$H$_{11}$-i | m.p. 84–86° C. |
| 254 | CH$_2$OH | OH | m.p. 147.1° C. |
| 255 | CH$_2$OH | OCH$_3$ | nD 1.5390 (21.4° C.) |
| 256 | CH$_2$O—CH=C(CN)(4-CH$_3$—Ph) | OC$_2$H$_5$ | m.p. 69–76° C. |
| 257 | CH$_2$N(CH$_3$)$_2$ | OCH$_3$ | m.p. 100.1° C. |
| 258 | CH$_2$N(CH$_3$)—Ph | OC$_2$H$_5$ | nD 1.5761 (24.2° C.) |
| 259 | CH$_2$NHCO-(2-COOH—Ph) | OH | m.p. 157.5° C. |
| 260 | CH$_2$—Q$_{10}$ | OCH$_3$ | nD 1.5335 (21.6° C.) |
| 261 | CH$_2$-(2,6-(CH$_3$)$_2$—Q$_{10}$) | O—Na | m.p. 73.7° C. |
| 262 | CH$_2$-(2,6-(CH$_3$)$_2$—Q$_{10}$) | OCH$_3$ | nD 1.5169 (21.6° C.) |
| 263 | CH$_2$—Q$_{16}$ | OCH$_3$ | m.p. 155.1° C. |
| 264 | CH$_2$—Q$_6$ | OCH$_3$ | paste NMR |
| 265 | CH$_2$—Q$_7$ | OCH$_3$ | paste NMR |
| 266 | Ph | OH | m.p. 148.5° C. |
| 267 | Ph | O—Na | NMR |
| 268 | Ph | OC$_2$H$_5$ | nD 1.5888 (20.8° C.) |
| 269 | Ph | NH$_2$ | m.p. 185.9° C. |
| 270 | Ph | NH—CH$_2$—CN | m.p. 147.1° C. |
| 271 | Ph | NH—CH(Q$_5$)—CN | m.p. 146.3° C. |
| 272 | 2-F—Ph | OH | m.p. 138.8° C. |
| 273 | 2-F—Ph | O—Na | NMR |
| 274 | 2-F—Ph | OCH$_3$ | nD 1.5611 (22.6° C.) |
| 275 | 2-F-4-Cl-5-OCH$_2$COOC$_2$H$_5$—Ph | OC$_2$H$_5$ | nD 1.5572 (21.5° C.) |
| 276 | CH$_2$O—Ph | OH | m.p. 153.9° C. |
| 277 | CH$_2$O—Ph | OCH$_3$ | nD 1.5772 (21.5° C.) |
| 278 | CH$_2$O(4-Cl—Ph) | OH | m.p. 148.2° C. |
| 279 | CH$_2$O(4-Cl—Ph) | OCH$_3$ | m.p. 72° C. |
| 280 | CH$_2$O(2-CH$_3$—Ph) | OH | m.p. 139.1–140.8° C. |
| 281 | CH$_2$O(2-CH$_3$—Ph) | OC$_2$H$_5$ | nD 1.5579 (20.1° C.) |
| 282 | CH$_2$ON=C(CH$_3$)(4-Cl—Ph) | OC$_2$H$_5$ | paste NMR |
| 283 | CH$_2$SO$_2$Ph | OH | m.p. 161–162° C. |
| 284 | CH$_2$SO$_2$Ph | OC$_2$H$_5$ | m.p. 75.6–77.8° C. |
| 285 | CH$_2$SO$_2$Ph | NHCH(CH$_3$)—Ph | m.p. 127–131° C. |
| 286 | CH$_2$S—Q$_{11}$ | OCH$_3$ | nD 1.6145 (24.2° C.) |
| 287 | CH$_3$ | NHN=C(CH$_3$)Q$_4$ | m.p. >280° C. |
| 288 | CH$_3$ | NHCH(OC$_2$H$_5$)COOC$_2$H$_5$ | m.p. 68.8° C. |
| 289 | CH$_3$ | NHCH(OC$_3$H$_7$-i)COOC$_2$H$_5$ | m.p. 52.1° C. |
| 290 | CH$_3$ | NHCH(Q$_5$)COOC$_2$H$_5$ | m.p. 107.3° C. |
| 291 | CH$_3$ | NHCH(OC$_2$H$_5$)CONH$_2$ | m.p. 136.9° C. |
| 292 | CH$_3$ | NHCH(CN)OCH$_2$COOC$_2$H$_5$ | nD 1.5217 (21.7° C.) |
| 293 | CH$_3$ | NHCH(CN)SCH$_2$COOC$_2$H$_5$ | nD 1.5525 (21.5° C.) |
| 294 | CH$_3$ | NHCH$_2$COOC$_2$H$_5$ | nD 1.5248 (21.5° C.) |
| 295 | CH$_3$ | NHCH(CCl$_3$)OH | m.p. 150° C. |
| 296 | CH$_3$ | NHCH(CCl$_3$)OC$_4$H$_9$-n | paste NMR |
| 297 | H | O—Na | |
| 298 | H | O—C$_3$H$_7$-i | |
| 299 | H | O—C$_6$H$_{13}$-n | |
| 300 | H | O—C$_{12}$H$_{25}$-n | |
| 301 | H | O—Ph | |
| 302 | H | O-(4-Cl—Ph) | |
| 303 | H | O-(4-CH$_3$—Ph) | |
| 304 | H | O—CH$_2$—Ph | |
| 305 | H | O—CH$_2$-(4-Cl—Ph) | |
| 306 | CH$_3$ | O—C$_4$H$_9$-i | |
| 307 | CH$_3$ | O—C$_6$H$_{13}$-n | |
| 308 | CH$_3$ | O-(2-Cl—Ph) | |
| 309 | CH$_3$ | O-(3-Cl—Ph) | |
| 310 | CH$_3$ | O-(2-OCH$_3$—Ph) | |
| 311 | CH$_3$ | O-(3-OCH$_3$—Ph) | |
| 312 | CH$_3$ | O-(2,4-(Cl)$_2$—Ph) | |
| 313 | CH$_3$ | O-(3,4-(Cl)$_2$—Ph) | |
| 314 | CH$_3$ | O-(3,5-(Cl)$_2$—Ph) | |
| 315 | CH$_3$ | O—CH$_2$-(2-Cl—Ph) | |
| 316 | CH$_3$ | O—CH$_2$-(3-Cl—Ph) | |
| 317 | CH$_3$ | O—CH$_2$-(2-CH$_3$—Ph) | |

TABLE 1-continued

| | | | |
|---|---|---|---|
| 318 | CH$_3$ | O—CH$_2$-(3-CH$_3$—Ph) | |
| 319 | CH$_3$ | O—CH$_2$-(3-OCH$_3$—Ph) | |
| 320 | CH$_3$ | O—C(CH$_3$)$_2$—Ph) | |
| 321 | CH$_3$ | O—(CH$_2$)$_3$O—CO(4-CH$_3$—Q$_8$) | |
| 322 | CH$_3$ | O—(CH$_2$)$_6$O—CO(4-CH$_3$—Q$_8$) | |
| 323 | CH$_3$ | O—(CH$_2$)$_{12}$O—CO(4-CH$_3$—Q$_8$) | |
| 324 | CH$_3$ | O—N=C(Cl)—Ph | |
| 325 | CH$_3$ | O—N=C(CN)—Ph | |
| 326 | CH$_3$ | O—N=C(CH$_3$)—C$_6$H$_{11}$-cyclo | |
| 327 | CH$_3$ | O—N=C(CH$_3$)—CH$_2$OCH$_3$ | |
| 328 | CH$_3$ | O—N=C(CH$_3$)—COOCH$_3$ | |
| 329 | CH$_3$ | O—N=C(COOC$_2$H$_5$)$_2$ | |
| 330 | CH$_3$ | O—N=C(SCH$_3$)—Ph | |
| 331 | CH$_3$ | O—N=C(S—Ph)—Ph | |
| 332 | CH$_3$ | O—N=C(Ph)—N(CH$_3$)$_2$ | |
| 333 | CH$_3$ | S—Ph | |
| 334 | CH$_3$ | S-(4-Cl—Ph) | |
| 335 | CH$_3$ | S-(4-OCH$_3$—Ph) | |
| 336 | CH$_3$ | S—CH$_2$-(4-CH$_3$—Ph) | |
| 337 | CH$_3$ | S—CH$_2$-(4-OCH$_3$—Ph) | |
| 338 | CH$_3$ | S—CH$_2$COOC$_2$H$_5$ | |
| 339 | CH$_3$ | S—Q$_2$ | |
| 340 | CH$_3$ | NH(3-C$_2$H$_5$—Ph) | m.p. 87.4–88.5° C. |
| 341 | CH$_3$ | NH(4-C$_2$H$_5$—Ph) | m.p. 95.1–96.2° C. |
| 342 | CH$_3$ | NH(2-COOC$_2$H$_5$—Ph) | m.p. 63° C. |
| 343 | CH$_3$ | NH(3-COOC$_2$H$_5$—Ph) | paste |
| 344 | CH$_3$ | NH(4-COOC$_3$H$_7$-i-Ph) | m.p. 125.2–127.5° C. |
| 345 | CH$_3$ | NH(2-CONH$_2$—Ph) | m.p. 222–223° C. |
| 346 | CH$_3$ | NH(3-CONH$_2$—Ph) | m.p. 232° C. |
| 347 | CH$_3$ | NH(4-CONH$_2$—Ph) | m.p. 244.8–248.2° C. |
| 348 | CH$_3$ | NH(2-CONHCH$_3$—Ph) | m.p. 162° C. |
| 349 | CH$_3$ | NH(3-CONHCH$_3$—Ph) | m.p. 181° C. |
| 350 | CH$_3$ | NH(4-CONHCH$_3$—Ph) | m.p. 196.3–198.1° C. |
| 351 | CH$_3$ | NH(2-CONHC$_2$H$_5$—Ph) | m.p. 166° C. |
| 352 | CH$_3$ | NH(3-CONHC$_2$H$_5$—Ph) | m.p. 155° C. |
| 353 | CH$_3$ | NH(4-CONHC$_2$H$_5$—Ph) | m.p. 190.8–193.4° C. |
| 354 | CH$_3$ | NH(2-CONHC$_3$H$_7$-n-Ph) | m.p. 165° C. |
| 355 | CH$_3$ | NH(3-CONHC$_3$H$_7$-n-Ph) | paste |
| 356 | CH$_3$ | NH(4-CONHC$_3$H$_7$-n-Ph) | m.p. 174.7–175.9° C. |
| 357 | CH$_3$ | NH(2-CONHC$_3$H$_7$-i-Ph) | m.p. 177° C. |
| 358 | CH$_3$ | NH(3-CONHC$_3$H$_7$-i-Ph) | m.p. 158° C. |
| 359 | CH$_3$ | NH(4-CONHC$_3$H$_7$-i-Ph) | m.p. 223.7–225.9° C. |
| 360 | CH$_3$ | NH(3-CONHC$_4$H$_9$-n-Ph) | paste |
| 361 | CH$_3$ | NH(4-CONHC$_4$H$_9$-n-Ph) | m.p. 157.4–159.3° C. |
| 362 | CH$_3$ | NH(3-CONHC$_4$H$_9$-t-Ph) | paste |
| 363 | CH$_3$ | NH(4-CONHC$_4$H$_9$-t-Ph) | m.p. 229.4–231.1° C. |
| 364 | CH$_3$ | NH(2-CONHPh—Ph) | m.p. 172–174° C. |
| 365 | CH$_3$ | NH(4-CONHPh—Ph) | m.p. 258.2–249.1° C. |
| 366 | CH$_3$ | NH(2-CON(CH$_3$)$_2$—Ph) | m.p. 153° C. |
| 367 | CH$_3$ | NH(3-CON(CH$_3$)$_2$—Ph) | m.p. 143° C. |
| 368 | CH$_3$ | NH(4-CON(CH$_3$)$_2$—Ph) | m.p. 176.8–178.6° C. |
| 369 | CH$_3$ | NH(3-CON(C$_2$H$_5$)$_2$—Ph) | paste |
| 370 | CH$_3$ | NH(4-CON(C$_2$H$_5$)$_2$—Ph) | m.p. 157.4–160.2° C. |
| 371 | CH$_3$ | NH(3-CONHC$_6$H$_{13}$-n-Ph) | paste |
| 372 | CH$_3$ | NH(3-CONH(4-Cl—Ph)—Ph) | paste |
| 373 | CH$_3$ | NH(3-CO—Q$_{10}$—Ph) | paste |
| 374 | CH$_3$ | NH(2-COOH—Ph) | m.p. 223° C. |
| 375 | CH$_3$ | NH(3-COOH—Ph) | m.p. 237° C. |
| 376 | CH$_3$ | NH(2-C$_3$H$_7$-n-Ph) | m.p. 76–78° C. |
| 377 | CH$_3$ | NH(4-C$_3$H$_7$-n-Ph) | m.p. 76–82° C. |
| 378 | CH$_3$ | NH(2-C$_3$H$_7$-i-Ph) | m.p. 116–118° C. |
| 379 | CH$_3$ | NH(4-C$_3$H$_7$-i-Ph) | m.p. 115–117° C. |
| 380 | CH$_3$ | NH(4-C$_4$H$_9$-n-Ph) | paste |
| 381 | CH$_3$ | NH(4-C$_4$H$_9$-sec-Ph) | m.p. 89–91° C. |
| 382 | CH$_3$ | NH(2-C$_4$H$_9$-t-Ph) | m.p. 114–115° C. |
| 383 | CH$_3$ | NH(4-C$_4$H$_9$-t-Ph) | paste |
| 384 | CH$_3$ | NH(4-C$_8$H$_{17}$-n-Ph) | m.p. 51–52° C. |
| 385 | CH$_3$ | NH(2-Br—Ph) | m.p. 139.8–142.1° C. |
| 386 | CH$_3$ | NH(3-Br—Ph) | m.p. 144.4–146.3° C. |
| 387 | CH$_3$ | NH(4-Br—Ph) | m.p. 122.9–124.4° C. |
| 388 | CH$_3$ | NH(2,6-Cl$_2$—Ph) | m.p. 168° C. |
| 389 | CH$_3$ | NH(2,3-Cl$_2$—Ph) | m.p. 151° C. |
| 390 | CH$_3$ | NH(2-C$_2$H$_5$—Ph) | m.p. 99.5–101.0° C. |
| 391 | CH$_3$ | NH(3,5-(CH$_3$)$_2$—Ph) | m.p. 135° C. |
| 392 | CH$_3$ | NH(2,3-(CH$_3$)$_2$—Ph) | m.p. 124° C. |
| 393 | CH$_3$ | NH(3,4-(CH$_3$)$_2$—Ph) | m.p. 116.8–118.2° C. |
| 394 | CH$_3$ | NH(2,5-(CH$_3$)$_2$—Ph) | m.p. 140° C. |
| 395 | CH$_3$ | NH(2,4-(OCH$_3$)$_2$—Ph) | m.p. 136° C. |
| 396 | CH$_3$ | NH(2,5-(OCH$_3$)$_2$—Ph) | m.p. 142° C. |

TABLE 1-continued

| | | | |
|---|---|---|---|
| 397 | $CH_3$ | $NH(3,4-(OCH_3)_2-Ph)$ | m.p. 133° C. |
| 398 | $CH_3$ | $NH(3,5-(OCH_3)_2-Ph)$ | m.p. 132° C. |
| 399 | $CH_3$ | $NH(4-OC_2H_5-Ph)$ | m.p. 105.9–106.7° C. |
| 400 | $CH_3$ | $NH(2-NH_2-Ph)$ | |
| 401 | $CH_3$ | $NH(3-NH_2-Ph)$ | m.p. 168° C. |
| 402 | $CH_3$ | $NH(4-NH_2-Ph)$ | m.p. 181° C. |
| 403 | $CH_3$ | $NH(4-CH_3CONH-Ph)$ | m.p. 206° C. |
| 404 | $CH_3$ | $NH(4-PhCONH-Ph)$ | m.p. 272° C. |
| 405 | $CH_3$ | $NH(4-(4-CH_3-Ph)SO_2NHPh)$ | m.p. 179° C. |
| 406 | $CH_3$ | $NH(2-NHCOCH_3-Ph)$ | |
| 407 | $CH_3$ | $NH(3-NHCOCH_3-Ph)$ | |
| 408 | $CH_3$ | $NH(4-NHCOC_2H_5-Ph)$ | |
| 409 | $CH_3$ | $NH(4-NHCOC_3H_7-i-Ph)$ | |
| 410 | $CH_3$ | $NH(2-NHCOC_4H_9-t-Ph)$ | |
| 411 | $CH_3$ | $NH(3-NHCOC_4H_9-t-Ph)$ | |
| 412 | $CH_3$ | $NH(4-NHCOC_4H_9-t-Ph)$ | |
| 413 | $CH_3$ | $NH(4-NHCOOCH_3-Ph)$ | |
| 414 | $CH_3$ | $NH(2-NHCOOC_2H_5-Ph)$ | |
| 415 | $CH_3$ | $NH(3-NHCOOC_2H_5-Ph)$ | |
| 416 | $CH_3$ | $NH(4-NHCOOC_2H_5-Ph)$ | |
| 417 | $CH_3$ | $NH(2-NHCOPh-Ph)$ | |
| 418 | $CH_3$ | $NH(3-NHCOPh-Ph)$ | |
| 419 | $CH_3$ | $NH(4-NHCO(6-Cl-Q_1)-Ph)$ | |
| 420 | $CH_3$ | $NH(2-NHCO(4-CH_3-Q_8)-Ph)$ | m.p. 189° C. |
| 421 | $CH_3$ | $NH(4-NHCO(4-CH_3-Q_8)-Ph)$ | m.p. 260° C. |
| 422 | $CH_3$ | $NH(4-NHCONHC_2H_5-Ph)$ | |
| 423 | $CH_3$ | $NH(2-NHSO_2CH_3-Ph)$ | |
| 424 | $CH_3$ | $NH(3-NHSO_2CH_3-Ph)$ | |
| 425 | $CH_3$ | $NH(4-NHSO_2CH_3-Ph)$ | |
| 426 | $CH_3$ | $NH(2-NO_2-Ph)$ | |
| 427 | $CH_3$ | $NH(3-NO_2-Ph)$ | m.p. 140° C. |
| 428 | $CH_3$ | $NH(2-OH-Ph)$ | |
| 429 | $CH_3$ | $NH(3-OH-Ph)$ | |
| 430 | $CH_3$ | $NH(4-OH-Ph)$ | |
| 431 | $CH_3$ | $NH(2-O-COCH_3-Ph)$ | |
| 432 | $CH_3$ | $NH(3-O-COCH_3-Ph)$ | |
| 433 | $CH_3$ | $NH(4-O-COCH_3-Ph)$ | |
| 434 | $CH_3$ | $NH(2-O-COC_4H_9-t-Ph)$ | |
| 435 | $CH_3$ | $NH(3-O-COC_4H_9-t-Ph)$ | |
| 436 | $CH_3$ | $NH(4-O-COC_4H_9-t-Ph)$ | |
| 437 | $CH_3$ | $NH(3-O-COPh-Ph)$ | |
| 438 | $CH_3$ | $NH(4-O-COPh-Ph)$ | |
| 439 | $CH_3$ | $NH(2-O-CO(4-CH_3-Q_8)-Ph$ | m.p. 112° C. |
| 440 | $CH_3$ | $NH(3-O-CO(4-CH_3-Q_8)-Ph$ | m.p. 152° C. |
| 441 | $CH_3$ | $NH(4-O-CO(4-CH_3-Q_8)-Ph$ | m.p. 167° C. |
| 442 | $CH_3$ | $NH(2-O-COOC_2H_5-Ph)$ | |
| 443 | $CH_3$ | $NH(3-O-COOC_2H_5-Ph)$ | |
| 444 | $CH_3$ | $NH(4-O-COOC_2H_5-Ph)$ | |
| 445 | $CH_3$ | $NH(4-O-COOC_2H_5-Ph)$ | |
| 446 | $CH_3$ | $NH(4-CH_3SO_2-Ph)$ | |
| 447 | $CH_3$ | $NH(4-CF_3SO_2-Ph)$ | |
| 448 | $CH_3$ | $NH(5-CH_3-Q_{18})$ | m.p. 156° C. |
| 449 | $CH_3$ | $NH(2-CH_3-Q_{19})$ | m.p. 189° C. |
| 450 | $CH_3$ | $NH(4,6-(CH_3)_2-Q_{11})$ | paste |
| 451 | $CH_3$ | $NHCH_2CONH(4-Cl-Ph)$ | m.p. 211° C. |
| 452 | $CH_3$ | $NHCH_2CONH(4-CH_3-Ph)$ | m.p. 212° C. |
| 453 | $CH_3$ | $NHCH_2CONH(4-OCH_3-Ph)$ | m.p. 188° C. |
| 454 | $CH_3$ | $NHCH_2CONHCH_2(4-CH_3-Ph)$ | paste |
| 455 | $CH_3$ | $Q_{20}-(4-CO(4-CH_3-Q_8))$ | m.p. 234° C. |
| 456 | $CH_3$ | $NH-(5-Br-Q_{11})$ | |
| 457 | $CH_3$ | $NH-(4,6-(Cl)_2-Q_{11})$ | |
| 458 | $CH_3$ | $NH-(4,6-(CH_3)_2-Q_{11})$ | m.p. 153° C. |
| 459 | $CH_3$ | $NH-Q_1$ | |
| 460 | $CH_3$ | $NH-Q_{21}$ | |
| 461 | $CH_3$ | $NH-(4-CH_3-Q_{21})$ | |
| 462 | $CH_3$ | $NH-(4-Ph-Q_{21})$ | |
| 463 | $CH_3$ | $NH-(5-CF_3-Q_{19})$ | |
| 464 | $CH_3$ | $NH-(5-SC_2H_5-Q_{19})$ | |
| 465 | $CH_3$ | $NH-(3-Cl-5-CF_3-Q_2)$ | |
| 466 | $CH_3$ | $NH-(4,6-(CH_3)_2-Q_2)$ | |
| 467 | $CH_3$ | $NH-Q_{22}$ | |
| 468 | $CH_3$ | $NH(CH_2)_2NH-CO(4-CH_3-Q_8)$ | |
| 469 | $CH_3$ | $NH(CH_2)_3NH-CO(4-CH_3-Q_8)$ | |
| 470 | $CH_3$ | $NH(CH_2)_6NH-CO(4-CH_3-Q_8)$ | |
| 471 | $CH_3$ | $NH(CH_2)_{12}NH-CO(4-CH_3-Q_8)$ | |
| 472 | $CH_3$ | $NH(Ph)-NH_2$ | |
| 473 | $CH_3$ | $NHNHPh$ | |
| 474 | $CH_3$ | $NHNHCOCH_3$ | |
| 475 | $CH_3$ | $NHNHCOC_6H_{13}-n$ | |

TABLE 1-continued

| | | | |
|---|---|---|---|
| 476 | CH₃ | NHNHCOC₁₂H₂₅-n | |
| 477 | CH₃ | NHNHCOCF₃ | |
| 478 | CH₃ | NHNHCO(4-Cl—Ph) | |
| 479 | CH₃ | NHNHCO(4-CH₃—Ph) | |
| 480 | CH₃ | NHNHCO(4-OCH₃—Ph) | |
| 481 | CH₃ | NHNHCOOCH₃ | |
| 482 | CH₃ | NHNHCOO—Ph | |
| 483 | CH₃ | NHNHCOO—CH₂Ph | |
| 484 | CH₃ | NHNHCONH₂ | |
| 485 | CH₃ | NHNHCONHCH₃ | |
| 486 | CH₃ | NHNHCONH—Ph | |
| 487 | CH₃ | NHNHSO₂CH₃ | |
| 488 | CH₃ | NHNHSO₂—Ph | |
| 489 | CH₃ | NHOC₂H₅ | |
| 490 | CH₃ | NHOC₃H₇-n | |
| 491 | CH₃ | NHOC₃H₇-i | |
| 492 | CH₃ | NHOC₄H₉-n | |
| 493 | CH₃ | NHOC₄H₉-t | |
| 494 | CH₃ | N(CH₃)OCH₃ | |
| 495 | CH₃ | NHOCH₂CH=CH₂ | |
| 496 | CH₃ | N(OH)(4-Cl—Ph) | m.p. 186° C. (decomp.) |
| 497 | CH₃ | N(OCH₃)(4-Cl—Ph) | m.p. 98° C. |
| 498 | CONH₂ | NH₂ | m.p. 270° C. (sublim.) |
| 499 | CH₃ | NH(3-Cl-4-CH₃—Ph) | m.p. 114° C. |

Note: "cyclo" means a cyclic C₆H₁₁ group.

Table 2 shows ¹H-NMR data of the 1,2,3-thiadiazole derivatives having a physical property expressed by the word "oil", "paste" or "NMR" in Table 1.

TABLE 2

| No | ¹H-NMR [CDCl₃/TMS, δ value (ppm) |
|---|---|
| 24 | 0.879(5, 3H), 1.255(br, 8H), 1.75(m, 2H), 2.974(m, 1H), 4.340(t, 2H). |
| 64 | 2.97(s, 6H), 4.68(s, 4H). |
| 96 | 1.595(s, 1H), 1.757(s, 6H), 2.910(s, 3H), 5.98 (br, 1H). |
| 97 | 1.305(d, 2H), 1.85(br, 1H), 2.903(s, 3H), 3.735(m, 2H), 4.25(m, 1H), 6.42(br, 1H). |
| 102 | 1.00(t, 6H), 2.30(m, 1H), 2.950(s, 3H), 3.800 (s, 3H), 4.740(m, 1H), 6.42(br, 1H). |
| 114 | 1.342(d, 6H), 2.948(s, 3H), 4.567(sept, 1H), 6.743(d, 1H), 7.011(d, 1H), 7.23–7.28(m, 2H), 7.659(s, 1H). |
| 118 | 1.2695(d, 6H), 2.9355(sept, 1H), 2.9868(s, 3H), 7.1260(d, 1H), 7.32–7.40(m, 3H), 7.47(br, s, 1H). |
| 140 | 2.818(s, 3H), 3.482(s, 3H), 7.11(m, 2H), 7.36 (m, 3H). |
| 144 | 2.792(s, 3H), 3.25(m, 1H), 3.822(s, 3H), 5.05 (m, 1H), 6.32(br, 1H), 7.05–7.40(m, 5H). |
| 150 | 1.26(t, 3H), 2.90(s, 3H), 3.74(q, 2H), 6.11 (d, 1H), 8.03(br, d, 1H). |
| 151 | 2.637(t, 3H), 2.971(s, 1H), 4.425(m, 2H), 6.374(d, 1H), 7.13(br, d, 1H). |
| 154 | 1.01(m, 3H), 1.39(q, 3H), 1.65(m, 2H), 2.94 (s, 3H), 3.10(m, 1H), 6.07(m, 1H), 7.05(br, t, 1H). |
| 186 | 1.33(d, 6H), 4.13(m, 1H). |
| 193 | 1.487(d, 6H), 3.73(sept, 1H), 4.365(d, 2H), 6.78(br, s, 1H) |
| 213 | 1.345(d, 6H), 4.568(s, 1H), 6.70–7.30(m, 4H), 7.92(br, s, 1H). |
| 227 | 1.20–1.40(m, 10H), 2.53(m, 1H), 2.89(m, 1H), 7.05–7.50(m, 4H), 8.30(br, s, 1H). |
| 228 | 1.20–1.40(m, 10H), 2.50(m, 1H), 4.55(m, 1H), 6.72(q, 1H), 7.0–7.3(m, 3H), 8.30(br, s, 1H). |
| 242 | 0.98(t, 3H), 1.49(m, 2H), 1.84(m, 2H), 4.50 (t, 2H), 4.63(d, 2H), 7.3–7.6(m, 5H), 10.23 (br, s, 1H). |
| 246 | 0.98(t, 3H), 1.49(m, 2H), 1.84(m, 2H), 4.50 (t, 2H), 4.63(d, 2H), 7.3–7.6(m, 5H), 10.23 (br, s, 1H). |
| 264 | 4.000(s, 3H), 5.854(s, 2H), 7.039(s, 1H), 7.142(s, 1H), 7.742(s, 1H). |
| 265 | 4.001(s, 3H), 6.104(s, 2H), 7.934(s, 1H), 8.378(s, 1H). |
| 267 | 7.3–7.5(m, 3H), 8.12(q, 2H) |
| 273 | 7.1–7.5(m, 4H) |
| 282 | 1.41(t, 3H), 2.27(s, 3H), 4.44(q, 2H), 5.88 (s, 2H), 7.2–7.6(m, 4H). |
| 296 | 0.939(t, 3H), 1.45(m, 2H), 1.65(m, 2H), 2.970 (s, 3H), 3.82(m, 2H), 5.75(d, 1H), 6.48(d, 1H). |
| 343 | 1.38(t, 3H), 2.96(s, 3H), 4.32(dd, 2H), 7.47 (t, 1H), 7.85(d, 1H), 8.00–8.05(br, 2H), 8.21 (br, 1H). |
| 355 | 0.86(t, 3H), 1.46(m, 2H), 2.87(s, 3H), 3.07 (dd, 2H), 6.43(m, 1H), 7.39(d, 2H), 7.97(br, 1H), 8.10(m, 1H), 9.75(br, 1H). |
| 360 | 0.92(t, 3H), 1.36(m, 2H), 1.51(m, 2H), 3.21 (dd, 2H), 6.21(br, 1H), 7.44(d, 2H), 7.98(s, 1H), 8.08(br, 1H), 9.19(br, 1H). |
| 362 | 1.36(s, 9H), 2.84(s, 3H), 6.05(s, 1H), 7.34 (m, 2H), 7.81(s, 1H), 7.90(m, 1H), 9.41(br, 1H). |
| 369 | 1.03–1.21(m, 6H), 3.19(dd, 2H), 3.41(dd, 2H), 6.87(d, 1H), 7.24(m, 2H), 7.73(d, 1H), 10.21 (br, 1H). |
| 371 | 0.89(t, 3H), 1.20–1.70(m, 8H), 3.24(dd, 2H), 6.21(br, 1H), 7.40–7.50(m, 1H), 7.99(s, 1H), 8.05(br, 1H), 9.01(br, 1H). |
| 372 | 2.95(s, 3H), 7.25–7.95(m, 7H), 8.06–8.14(br, 2H), 8.56(br, 1H). |
| 373 | 2.89(s, 3H), 3.4–3.8(br, 8H), 7.02(d, 1H), 7.35(t, 1H), 7.47(br, 1H), 7.87(d, 1H), 9.53 (br, 1H). |
| 380 | 0.93(t, 3H), 1.37(m, 2H), 1.59(m, 2H), 2.61 (t, 2H), 2.97(s, 1H), 7.22(d, 2H), 7.45(d, 2H), 7.53(br, 1H). |
| 383 | 1.32(s, 9H), 2.96(s, 3H), 7.34(d, 2H), 7.49 (d, 2H), 7.88(d, 1H). |
| 450 | 2.42(s, 6H), 2.90(s, 3H), 6.82(s, 1H), 8.6–9.5 (br, 1H). |
| 454 | 2.28(s, 3H), 2.81(s, 3H), 3.92(d, 2H), 4.26 (d, 2H), 7.12(m, 4H), 8.51(br, 1H), 9.08(br, 1H). |

The 1,2,3-thiadiazole derivatives of the general formula (I) or salts thereof according to the present invention are useful for agricultural and horticultural disease control. For example, the compounds listed in Table 1 are very effective in controlling various diseases, for instance, rice blast (*Pyricularia oryzae*), rice sheath blight (*Rhizoctonia solani*), rice helminthosporium leaf spot (*Cochliobolus miyabeanus*), powdery mildew of various host plants, such as powdery mildew of barley and wheat (*Erysiphe graminis*), oats crown rust (*Puccinia coronata*), rust of other plants, tomato late blight (*Phytophthora infestans*), late blight or Phytophthora rots of other plants, downy mildew of plants, such as cucumber downy mildew (*Pseudoperonospora cubensis*) and grape downy mildew (*Plasmopara viticola*), apple scab (*Venturia inaequalis*), apple alternaria leaf spot (*Alternaria mali*), pear black spot (*Alternaria kikuchiana*), citrus melanose (*Diaporthe citri*), cucumber bacterial blight (*Pseudomonas syringae* pv. *lachrymans*), tomato bacterial wilt (*Pseudomonas solanacearum*), cabbage black rot (*Xanthomonas campestris*), citrus canker (*Xanthomonas citri* (Hasse) Dowson), rice bacterial leaf blight (*Xanthomonas oryzae*), cabbage bacterial soft rot (*Erwinia carotovora*), and tobacco mosaic (Tobacco mosaic virus).

The agricultural and horticultural disease controller of the present invention is markedly effective in controlling the above-exemplified diseases which damage paddy field crops, upland crops, fruit trees, vegetables, other crops, flowers and ornamental plants, and the like. Therefore, the desired effects of the agricultural and horticultural disease controller of the present invention can be obtained by applying the disease controller to the paddy field water, stalks and leaves of fruit trees, vegetables, other crops, flowers and ornamental plants, soil, etc., at a season at which the diseases are expected to occur, before their occurrence or at the time when their occurrence is confirmed.

In general, the agricultural and horticultural disease controller of the present invention is used after being prepared into a conveniently usable form according to an ordinary manner for preparation of agrochemicals.

That is, the 1,2,3-thiadiazole derivative of the general formula (I) or salt thereof according to the present invention and, optionally, an adjuvant are blended with a suitable inert carrier in a proper proportion and prepared into a suitable preparation form such as a suspension, emulsifiable concentrate, soluble concentrate, wettable powder, granules, dust or tablets through dissolution, dispersion, suspension, mixing, impregnation, adsorption or sticking.

The inert carrier used in the present invention may be either solid or liquid. As the solid carrier, there can be exemplified soybean flour, cereal flour, wood flour, bark flour, saw dust, powdered tobacco stalks, powdered walnut shells, bran, powdered cellulose, extraction residue of vegetables, powdered synthetic polymers or resins, clays (e.g. kaolin, bentonite, and acid clay), talcs (e.g. talc and pyrophyllite), silica powders or flakes (e.g. diatomaceous earth, silica sand, mica and white carbon, i.e. synthetic, high-dispersion silicic acid, also called finely divided hydrated silica or hydrated silicic acid, some of commercially available products contain calcium silicate as the major component), activated carbon, powdered sulfur, powdered pumice, calcined diatomaceous earth, ground brick, fly ash, sand, calcium carbonate powder, calcium phosphate powder and other inorganic or mineral powders, chemical fertilizers (e.g. ammonium sulfate, ammonium phosphate, ammonium nitrate, urea and ammonium chloride), and compost. These carriers may be used alone or as a mixture thereof.

The liquid carrier is that which itself has solubility or which is without such solubility but is capable of dispersing an active ingredient with the aid of an adjuvant. The following are typical examples of the liquid carrier and can be used alone or as a mixture thereof. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, Cellosolve, dipropyl ether and tetrahydrofuran; aliphatic hydrocarbons such as kerosene and mineral oils; aromatic hydrocarbons such as benzene, toluene, xylene, solvent naphtha and alkylnaphthalenes; halogenated hydrocarbons such as dichloroethane, chloroform, carbon tetrachloride and chlorobenzene; esters such as ethyl acetate, diisopropyl phthalate, dibutyl phthalate and dioctyl phthalate; amides such as di-methylformamide, diethylformamide and dimethylacetamide; nitriles such as acetonitrile; and dimethyl sulfoxide.

The following are typical examples of the adjuvant, which are used depending upon purposes and used alone or in combination in some cases, or need not to be used at all.

To emulsify, disperse, dissolve and/or wet an active ingredient, a surfactant is used. As the surfactant, there can be exemplified polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates and higher alcohol sulfate esters.

Further, to stabilize the dispersion of an active ingredient, tackify it and/or bind it, there may be used adjuvants such as casein, gelatin, starch, methyl cellulose, carboxymethyl cellulose, gum arabic, polyvinyl alcohols, turpentine, bran oil, bentonite and ligninsulfonates.

To improve the flowability of a solid product, there may be used adjuvants such as waxes, stearates and alkyl phosphates.

Adjuvants such as naphthalenesulfonic acid condensation products and polycondensates of phosphates may be used as a peptizer for dispersible products.

Adjuvants such as silicon oils may also be used as a defoaming agent.

The content of the active ingredient may be varied as required. In dusts or granules, the suitable content thereof is from 0.01 to 50% by weight. In emulsifiable concentrates or flowable wettable powders, it is also from 0.01 to 50% by weight.

The present inventive agricultural and horticultural disease controller containing the 1,2,3-thiadiazole derivative of the general formula (I) or a salt thereof as an active ingredient is used to control various diseases in the following manner. That is, it is applied to a crop on which the diseases are expected to occur, or a site where the occurrence of the diseases is undesirable, as it is or after being properly diluted with or suspended in water or the like, in an amount effective for control of the diseases. For example, to control the diseases of paddy rice, said disease controller can be used by a method such as submerged application to a regular paddy field, application to a rice nursery bed, dressing of seeds for direct sowing on flooded paddy field, or seed disinfection.

The applying dosage of the present inventive agricultural and horticultural disease controller containing the 1,2,3-thiadiazole derivative of the general formula (I) or a salt thereof as an active ingredient is varied depending upon various factors such as a purpose, diseases to be controlled, a growth state of a plant, tendency of disease occurrence, weather, environmental conditions, a preparation form, an application method, an application site and application time. It may be properly chosen in the range of 0.1 g to 10 kg (in terms of the active ingredient) per 10 ares depending upon purposes.

The present inventive agricultural and horticultural disease controller containing the 1,2,3-thiadiazole derivative of the general formula (I) or a salt thereof as an active ingredient may be used in admixture with other agricultural and horticultural disease controllers in order to expand both spectrum of controllable diseases and the period of time when effective applications are possible or to reduce the dosage.

Typical examples and test examples of the present invention are described below but they should not be construed as limiting the scope of the invention.

In the examples, parts are all by weight.

EXAMPLE 1

| Each compound listed in Table 1 | 50 parts |
|---|---|
| Xylene | 40 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

EXAMPLE 2

| Each compound listed in Table 1 | 3 parts |
|---|---|
| Clay powder | 82 parts |
| Diatomaceous earth powder | 15 parts |

A dust was prepared by mixing uniformly and grinding the above ingredients.

EXAMPLE 3

| Each compound listed in Table 1 | 5 parts |
|---|---|
| Mixed powder of bentonite and clay | 90 parts |
| Calcium lignin sulfonate | 5 parts |

Granules were prepared by mixing the above ingredients uniformly, and kneading the resulting mixture together with a suitable amount of water, followed by granulation and drying.

EXAMPLE 4

| Each compound listed in Table 1 | 20 parts |
|---|---|
| Mixture of kaolin and synthetic, high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1
Controlling Effect on Rice Blast by Submerged Application

Rice plants at the 5 to 6 leaf stage cultivated in a 1/10000-are pot were subjected to submerged application of a chemical containing each compound listed in Table 1 as an active ingredient, in a dosage of 200 g/10 a in terms of the active ingredient. After standing in a greenhouse for 1 week, the plants were inoculated with a suspension of spores of blast fungus (*Pyricularia oryzae*) by spraying.

After the inoculation, the plants were allowed to stand in a moist chamber for 1 day and then a greenhouse for 6 days to cause the disease sufficiently. Then, lesions in each leaf were counted and then compared with those on the untreated plot, and the controlling degree was calculated, whereby the effect was judged according to the following criterion.

| Effect | Controlling degree (%) |
|---|---|
| A | 100–95 |
| B | 94–85 |
| C | 84–60 |
| D | 59–0 |

As a result of the above test, the compounds listed in Table 1 were found to have a marked blast-controlling activity. Of these compounds, the following were rated C or higher: compound Nos. 1 to 42, 44 to 61, 62 to 89, 92 to 95, 97 to 100, 103 to 131, 133 to 136, 138 to 140, 142, 144 to 166, 168 to 192, 194 to 196, 198 to 200, 202 to 222, 224, 225, 227 to 233, 237, 240 253 to 255, 268, 269, 272, 273, 276, 278, 287 to 296, 342 to 346, 348, 351, 354 to 357, 361, 362, 366, 369, 372, 374 and 375. In particular, the following were rated A, namely, the following had an excellent blast-controlling activity: compound Nos. 1, 3, 5 to 19, 21, 24 to 26, 28, 29, 32, 33, 37 to 40, 52, 54, 55, 57 to 59, 64 to 68, 70 to 74, 77 to 80, 84, 92, 93, 99, 103, 104 to 121, 123 to 125, 128, 130, 131, 138, 145, 146, 149, 152, 153, 156, 157, 159, 160, 169, 172 to 174, 175 to 192, 194, 198, 199, 202, 208 to 210, 213, 215 to 221, 224, 225, 227 to 229, 233, 237, 253, 278, 288 to 290, 294, 343, 344, 346, 355, 356, 362, 372, 374 and 375.

Test Example 2
Controlling Effect on Barley Powdery Mildew

Barley plants at the 3.5 leaf stage cultivated in a pot were applied with a spray mix containing each compound listed in Table 1 as an active ingredient at the concentration of 200 ppm. After standing thus treated plants in a greenhouse for 1 week, the plants were inoculated with spores of powdery mildew fungus (*Erysiphe graminis* f. sp. *hordei*)

After the inoculation, the plants were allowed to stand in a greenhouse for 1 week to cause the disease sufficiently. Then, lesions in each leaf were counted and then compared with those on the untreated plot, and the controlling degree was calculated, whereby the effect was judged according to the following criterion.

| Effect | Controlling degree (%) |
|---|---|
| A | 100–80 |
| B | 79–60 |
| C | 59–0 |

As a result of the above test, the compounds listed in Table 1 were found to have a marked powdery mildew-controlling activity. Of these compounds, the following were rated B or higher: compound Nos. 7 to 9, 15, 16, 33, 40, 66, 72, 84, 104 to 107, 111 to 113, 115 to 117, 122 to 124, 128, 130, 139, 145, 180, 193, 194, 215, 217, 218 and 224. In particular, the following were rated A: compound Nos. 7 to 9, 15, 16, 33, 40, 66, 72, 84, 104 to 107, 111 to 113, 115 to 117, 122 to 124, 128, 130, 139, 145, 180, 193, 215, 217, 218 and 224.

Referential Production Example 1

Production of sodium 4-ethyl-1,2,3-thiadiazole-5-carboxylate (Compound No. 8)

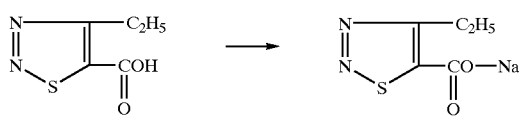

To a solution of 0.13 g of sodium hydroxide in 3 ml of ethanol was added 0.5 g of 4-ethyl-1,2,3-thiadiazole-5-carboxylic acid, and the reaction was carried out at room temperature for 24 hours.

After completion of the reaction, the solvent was distilled off under reduced pressure and the crude product thus obtained was recrystallized from ethanol to obtain 0.44 g of the desired-compound.

Physical property: m.p. 250° C. (decomp.).

Yield: 77%.

Referential Production Example 2

Production of t-butylammonium 4-ethyl-1,2,3-thiadiazole-5-carboxylate (Compound No. 185)

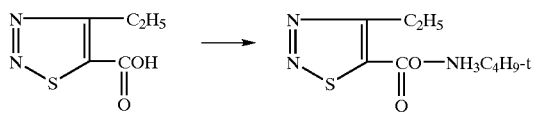

In 3 ml of ethanol was dissolved 0.4 g of 4-ethyl-1,2,3-thiadiazole-5-carboxylic acid, after which 0.19 g of t-butylamine was added to the solution and the reaction was carried out at room temperature for 24 hours.

After completion of the reaction, the crystals precipitated in the reaction solution were collected by filtration and washed with n-hexane to obtain 0.54 g of the desired compound.

Physical property: m.p. 105–107° C.

Yield: 93%.

Referential Production Example 3

Production of N-isopropyl-5-(N'-isopropyl-carbamoyl)-1,2,3-thiadiazol-4-ylacetamide (Compound No. 252)

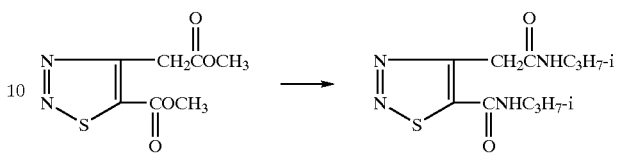

In dimethyl sulfoxide was suspended 0.1 g of sodium hydride, after which 1 g of isopropylamine was added to the suspension, followed by ice-cooling. Then, 0.5 g of methyl 5-methoxycarbonyl-1,2,3-thiadiazol-4-ylacetate was added and the resulting mixture was stirred at room temperature and allowed to stand for 24 hours.

After completion of the reaction, the reaction mixture was poured into ice water and the desired compound was extracted with ethyl acetate. The extracted solution was washed with water, dried over anhydrous sodium sulfate, and then distilled under reduced pressure to remove the solvent. The crude product thus obtained was purified by a column chromatography to obtain 0.23 g of the desired compound.

Physical property: m.p. 146–156° C.

Yield: 37%.

Referential Production Example 4

Production of ethyl 4-(2-methylphenoxymethyl)-1,2,3-thiadiazole-5-carboxylate (Compound No. 281)

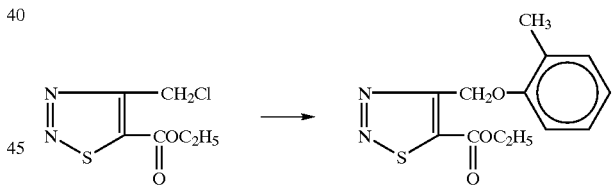

In 20 ml of dimethylformamide was suspended 0.5 g of sodium hydride, after which 1.57 g of 2-methylphenol was added to the suspension and the resulting mixture was stirred at room temperature for 5 minutes. The reaction mixture was cooled with ice, followed by adding thereto 3 g of ethyl 4-chloromethyl-1,2,3-thiadiazolecarboxylate, and the resulting mixture was stirred at room temperature and allowed to stand for 24 hours.

After completion of the reaction, the reaction mixture was poured into ice water and the desired compound was extracted three times with ethyl acetate. The extracted solution was washed with water, dried over anhydrous sodium sulfate, and then distilled under reduced pressure to remove the solvent, whereby 1.33 g of the desired compound was obtained.

Physical property: nD 1.5579 (20.1° C.).

Yield: 33%.

Referential Production Example 5

Production of isopropyl 4-methyl-1,2,3-thiadiazole-5-carboxylate (Compound No. 18)

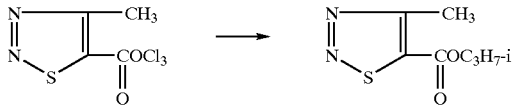

To 1.0 g (6.9 mmoles) of 4-methyl-1,2,3-thiadiazole-5-carboxylic acid were added 40 ml of thionyl chloride and 2 drops of dimethylformamide at room temperature, and the resulting mixture was refluxed with heating or 3 hours. After completion of the reaction, the reaction mixture was cooled to room temperature, and the excess thionyl chloride was distilled off and 7.0 ml of tetrahydrofuran was added to the residue. Then, 2.1 g (21 mmoles) of triethylamine and 0.83 g (13.8 mmoles) of isopropanol were added and the resulting mixture was stirred at room temperature for 18 hours, after which a saturated aqueous sodium chloride solution was added. The desired compound was extracted with ethyl acetate and the organic layer was washed successively with diluted hydrochloric acid, a saturated aqueous sodium hydrogencarbonate solution and a saturated aqueous sodium chloride solution, dried over anhydrous sodium sulfate, and then concentrated under reduced pressure. The resulting residue was purified by a silica gel column chromatography (n-hexane:ethyl acetate=10:1) to obtain 1.0 g of the desired compound.

Physical property: nD 1.4400 (14.3° C.).

Yield: 79%.

What is claimed is:

1. A method for controlling agricultural and horticultural diseases of plants which comprises applying a 1,2,3 thiadiazole derivative represented by the general formula (I), or a salt thereof at an active amount to control said plant diseases:

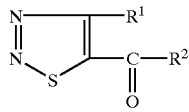 (I)

wherein $R^1$ is ① a hydrogen atom, ② a $(C_1-C_{12})$alkyl group, ③ a halo$(C_1-C_{12})$alkyl group, ④ a $(C_2-C_{12})$-alkenyl group, ⑤ a halo$(C_2-C_{12})$alkenyl group, ⑥ a $(C_2-C_{12})$alkynyl group, a halo$(C_2-C_{12})$alkynyl group, ⑧ a $(C_3-C_6)$cycloalkyl group, ⑨ an unsubstituted phenyl group, ⑩ a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups, ⑪ a group represented by the formula:

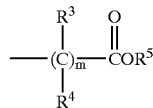

(wherein $R^3$ and $R^4$, which may be the same or different, are hydrogen atoms, $(C_1-C_{12})$alkyl groups or halo$(C_1-C_{12})$ alkyl groups, m is zero or an integer of 1 to 6, and $R^5$ is a hydrogen atom; a $(C_1-C_{12})$alkyl group; a halo$(C_1-C_{12})$alkyl group; a $(C_2-C_{12})$alkenyl group; a $(C_2-C_{12})$alkynyl group; an unsubstituted phenyl group; a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo $(C_1-C_6)$alkylthio groups, $(C_2-C_6)$alkenyl groups and $(C_2-C_6)$alkynyl groups; an unsubstituted phenyl$(C_1-C_6)$ alkyl group; or a substituted phenyl$(C_1-C_6)$alkyl group having on the ring one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$ alkoxy groups, halo$(C_1-C_6)$alkoxy groups, $(C_1-C_6)$ alkylthio groups, halo$(C_1-C_6)$alkylthio groups, $(C_2-C_6)$ alkenyl groups and $(C_2-C_6)$alkynyl groups), ⑫ a group represented by the formula:

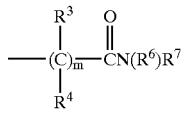

(wherein $R^3$, $R^4$ and m are as defined above, and $R^6$ and $R^7$, which may be the same or different, are hydrogen atoms; $(C_1-C_{12})$alkyl groups; halo$(C_1-C_{12})$alkyl groups; $(C_2-C_{12})$ alkenyl groups; $(C_2-C_{12})$alkynyl groups; $(C_1-C_{12})$alkoxy $(C_1-C_6)$alkyl groups; $(C_1-C_{12})$alkylthio $(C_1-C_6)$alkyl groups; cyano$(C_1-C_{12})$alkyl groups; unsubstituted phenyl groups; substituted phenyl groups having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups; unsubstituted phenyl$(C_1-C_6)$alkyl groups; or substituted phenyl $(C_1-C_6)$alkyl groups having on the ring one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups; $R^6$ and $R^7$ being able to be taken together to represent a $(C_4-C_6)$ alkylene group which may contain an oxygen atom between adjacent carbon atoms of the carbon chain), ⑬ a group represented by the formula:

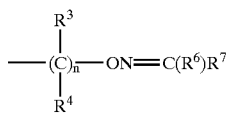

(wherein $R^3$, $R^4$, $R^6$ and $R^7$ are as defined above, and n is an integer of 1 to 6), or ⑭ a group represented by the formula:

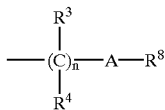

{{wherein $R^3$, $R^4$ and n are as defined above, A is

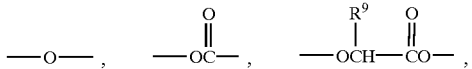

(wherein $R^9$ is a hydrogen atom, a $(C_1-C_{12})$alkyl group or a halo$(C_1-C_{12})$alkyl group),

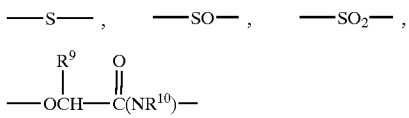

{wherein $R^9$ is as defined above, and $R^{10}$ is a hydrogen atom, a $(C_1-C_{12})$alkyl group or a halo$(C_1-C_{12})$alkyl group, $R^9$ and $R^{10}$ being able to be taken together to represent a $(C_4-C_6)$alkylene group which may contain, between adjacent carbon atoms of the carbon chain, an oxygen atom, a sulfur atom or

(wherein $R^{11}$ is a hydrogen atom, a $(C_1-C_{12})$alkyl group or a halo$(C_1-C_{12})$alkyl group)}, or

(wherein $R^{10}$ is as defined above), and $R^8$ is a hydrogen atom; a $(C_1-C_{12})$alkyl group; a halo$(C_1-C_{12})$alkyl group; a $(C_2-C_{12})$alkenyl group; a $(C_2-C_{12})$alkynyl group; a $(C_1-C_{12})$alkoxy$(C_1-C_{12})$alkyl group; a $(C_1-C_{12})$alkylthio-$(C_1-C_{12})$alkyl group; a cyano$(C_1-C_{12})$alkyl group; an unsubstituted phenyl group; a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups; an unsubstituted phenyl$(C_1-C_6)$-alkyl group; a substituted phenyl$(C_1-C_6)$alkyl group having on the ring one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkyl-thio groups, halo$(C_1-C_6)$alkylthio groups, $(C_2-C_6)$alkenyl groups and $(C_2-C_6)$alkynyl groups; an unsubstituted 5- or 6-membered heterocyclic ring having one or more heteroatoms which may be the same or different and are selected from the group consisting of oxygen atom, sulfur atom and nitrogen atom; or a substituted 5- or 6-membered heterocyclic ring having one or more heteroatoms which may be the same or different and are selected from the group consisting of oxygen atom, sulfur atom and nitrogen atom, said substituted heterocyclic ring having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkyl-thio groups, halo $(C_1-C_6)$alkylthio groups, $(C_2-C_6)$alkenyl groups and $(C_2-C_6)$alkynyl groups}}, and $R^2$ is (i) a group represented by the formula:

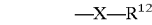

wherein X is an oxygen atom or a sulfur atom, and $R^{12}$ is ① a hydrogen atom, ② a $(C_1-C_{12})$alkyl group, ③ a halo$(C_1-C_{12})$alkyl group, ④ a $(C_2-C_{20})$alkenyl group, ⑤ a halo$(C_2-C_{20})$alkenyl group, ⑥ a $(C_2-C_{12})$alkynyl group, ⑦ a halo$(C_2-C_{12})$alkynyl group, ⑧ a hydroxy$(C_1-C_6)$alkyl group, ⑨ a $(C_1-C_{12})$alkoxy$(C_1-C_{12})$alkyl group, ⑩ a $(C_1-C_{12})$alkylthio$(C_1-C_{12})$alkyl group, ⑪ a $(C_3-C_6)$cycloalkyl group, ⑫ a $(C_3-C_6)$cycloalkyl$(C_1-C_{12})$alkyl group, ⑬ an unsubstituted phenyl group, a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups, $(C_2-C_6)$alkynyl groups, and $(C_1-C_6)$alkoxy carbonyl$(C_1-C_6)$alkyloxy groups ⑮ an unsubstituted phenyl$(C_1-C_6)$alkyl group, ⑯ a substituted phenyl $(C_1-C_6)$alkyl group having on the ring one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups, ⑰ a diphenyl$(C_1-C_6)$alkyl group, ⑱ a phenoxy$(C_1-C_6)$alkyl group, ⑲ a group represented by the formula:

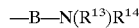

{wherein B is a $(C_1-C_6)$alkylene group which may be substituted by a $(C_1-C_6)$alkyl group or a phenyl group, and $R^{13}$ and $R^{14}$, which may be the same or different, are hydrogen atoms; formyl groups; $(C_1-C_{12})$alkyl groups; $(C_2-C_{12})$alkenyl groups; $(C_2-C_{12})$alkynyl groups;$(C_2-C_{12})$-alkylcarbonyl groups; unsubstituted phenyl groups; substituted phenyl groups having one or more substituents which may be the same or different and are selected from the group consisting of hydrogen atom, halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl, groups; phenylcarbonyl groups; unsubstituted 1,2,3-thiadiazol-5-yl-carbonyl groups; or substituted 1,2,3-thiadiazol-5-yl-carbonyl groups having a halogen atom or a $(C_1-C_6)$alkyl group as the substituent; $R^{13}$ and $R^{14}$ being able to be taken together to represent a $(C_4-C_5)$alkylene group which may contain, between adjacent carbon atoms of the carbon chain, an oxygen atom, a sulfur atom or

(wherein $R^{11}$ is as defined above)), ⑳ a group represented by the formula:

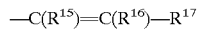

(wherein $R^{15}$ is a hydrogen atom or a $(C_1-C_6)$alkyl group, $R^{16}$ is a hydrogen atom, a halogen atom or a $(C_1-C_6)$alkyl group, and $R^{17}$ is a nitro group, a cyano group, a $(C_1-C_6)$alkylcarbonyl group, a $(C_1-C_6)$alkoxycarbonyl group, a phenylcarbonyl group, or a substituted aminocarbonyl group having one or more substituents which may be the same or different and are selected from the group consisting of hydrogen atom, ($C_1$–$C_{12}$)alkyl groups, unsubstituted phenyl group, and substituted phenyl groups having one or more substituents which may be the same or different and are selected from the group consisting of halogen atoms, cyano group, nitro group, ($C_1$–$C_6$)alkyl groups and ($C_1$–$C_6$)alkoxy groups, $R^{15}$ and $R^{17}$ being able to be taken together to represent a ($C_3$–$C_4$)alkylene group which may be substituted by one or more ($C_1$–$C_6$)alkyl group and/or an oxo group), ㉑ a group represented by the formula:

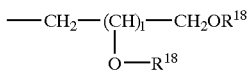

(wherein two $R^{18}$'s which may be the same or different, are hydrogen atoms, ($C_1$–$C_6$)alkylcarbonyl groups, phenylcarbonyl groups, unsubstituted 1,2,3-thiadiazol-5-yl-carbonyl groups, or substituted 1,2,3-thiadiazol-5yl-carbonyl groups having a halogen atom or a ($C_1$–$C_6$)alkyl group as the substituent, and l is zero or an integer of 1 to 12), ㉒ a 5- or 6-membered heterocyclic alkyl group having one or more heteroatoms which may be the same or different and are selected from the group consisting of oxygen atom, sulfur atom and nitrogen atom, ㉓ tri($C_1$–$C_6$)alkylsilyl($C_1$–$C_6$)alkyl groups, or ㉔ 1,2,3-thiadiazol-5-yl-carbonyloxy-($C_1$–$C_{12}$)alkyl groups having on the ring a halogen atom or ($C_1$–$C_6$)alkyl group as the substituent ㉕ ($C_1$–$C_6$)alkylcarbonyl($C_1$–$C_6$)alkyol groups or ㉖ ($C_1$–$C_6$)alkoxycarbonyl($C_1$–$C_6$)alkyl groups}}, (ii) a group represented by the formula:

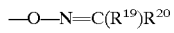

{{wherein $R^{19}$ and $R^{20}$, which may be the same or different, are ① hydrogen atoms, ② halogen atoms, ③ nitro groups, ④ cyano groups, ⑤ ($C_1$–$C_{12}$)alkyl groups, ⑥ halo($C_1$–$C_{12}$)alkyl groups, ⑦ ($C_3$–$C_6$)cycloalkyl groups, ⑧ ($C_2$–$C_{12}$)alkenyl groups, ⑨ ($C_2$–$C_{12}$)alkynyl groups, ⑩ ($C_1$–$C_{12}$)alkoxy($C_1$–$C_{12}$)alkyl groups, ⑪ ($C_1$–$C_{12}$)alkoxycarbonyl groups, ⑫ unsubstituted phenyl groups, ⑬ substituted phenyl groups having one or more substituents which may be the same or different and are selected from the group consisting of halogen atoms, nitro group, cyano group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio, groups, halo($C_1$–$C_6$)alkylthio groups, ($C_2$–$C_6$)alkenyl groups and ($C_2$–$C_6$)alkynyl groups, ⑭ unsubstituted 5- or 6-membered heterocyclic rings having one or more heteroatoms which may be the same or different and are selected from the group consisting of oxygen atom, sulfur atom and nitrogen atom, ⑮ substituted 5- or 6-membered heterocyclic rings having one or more heteroatoms which may be the same or different and are selected from the group consisting of oxygen atom, sulfur atom and nitrogen atom, said substituted heterocyclic ring having one or more substituents which may be the same or different and are selected from the group consisting of halogen atoms, nitro group, cyano group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_2$–$C_6$)alkenyl groups and ($C_2$–$C_6$)alkynyl groups, ⑯ groups represented by the formula;

(wherein $R^5$ is as defined above), or ⑰ groups represented by the formula:

(wherein $R^6$ and $R^7$ are as defined above), $R^{19}$ and $R^{20}$ being able to be taken together to represent ⑱ a ($C_3$–$C_6$)cycloalkane ring or a 5- or 6-membered heterocyclic ring containing, between adjacent carbon atoms of the carbon chain, one or more hetero atoms which may be the same or different and are selected from the group consisting of oxygen atom, sulfur atom and nitrogen atom}}, (iii) a group represented by the formula:

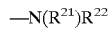

{{wherein $R^{21}$ and $R^{22}$, which may be the same or different, are ② ($C_1$–$C_{12}$)alkyl groups, ③ unsubstituted halo($C_1$–$C_{12}$)alkyl groups, ④ substituted halo($C_1$–$C_{12}$)alkyl groups having a hydroxyl group or a ($C_1$–$C_6$)alkoxy group as the substituent, ⑤ ($C_2$–$C_{12}$)alkenyl groups, ⑥ ($C_2$–$C_{12}$)alkynyl groups, ⑦ ($C_1$–$C_{12}$)alkoxy($C_1$–$C_6$)alkyl groups, ⑧ ($C_1$–$C_{12}$)alkylthio-($C_1$–$C_6$)alkyl groups, ⑨ cyano($C_1$–$C_{12}$)alkyl groups, ⑩ substituted cyano($C_1$–$C_6$)alkyl groups having on the alkyl chain a substituent selected from the group consisting of ($C_1$–$C_6$)alkoxy groups, ($C_2$–$C_6$)alkenyloxy groups, ($C_2$–$C_6$)alkynyloxy groups, ($C_1$–$C_6$)alkylthio groups, ($C_1$–$C_6$)alkoxycarbonyl($C_1$–$C_6$)alkoxy groups, ($C_1$–$C_6$)alkoxycarbonyl($C_1$–$C_6$)alkylthio groups, phenoxy group, phenylthio group and pyrazol-1-yl group, ⑪ unsubstituted carbamoyl($C_1$–$C_6$)alkyl groups, ⑫ substituted carbamoyl($C_1$–$C_6$)alkyl groups having on the alkyl chain a substituent selected from the group consisting of ($C_1$–$C_6$)alkoxy groups, ($C_2$–$C_6$)alkenyloxy groups, ($C_2$–$C_6$)alkynyloxy groups, ($C_1$–$C_6$)alkylthio groups, ($C_1$–$C_6$)alkoxycarbonyl($C_1$–$C_6$)alkoxy groups, ($C_1$–$C_6$)alkoxycarbonyl($C_1$–$C_6$)alkylthio groups, phenoxy group, phenylthio group and pyrazol-1-yl group, ⑬ hydroxy($C_1$–$C_6$)alkyl groups, di($C_1$–$C_6$)alkoxy($C_1$–$C_6$)alkyl groups in which the ($C_1$–$C_6$)alkoxy groups may be the same or different, ⑮ unsubstituted ($C_1$–$C_6$)alkoxycarbonyl($C_1$–$C_6$) alkyl groups, ⑯ substituted ($C_1$–$C_6$)alkoxy-carbonyl ($C_1$–$C_6$)alkyl groups having on the alkyl chain a substituent selected from the group consisting of ($C_1$–$C_6$)alkyl groups, ($C_1$–$C_6$)alkoxy groups, ($C_2$–$C_6$)alkenyloxy groups, ($C_2$–$C_6$)alkynyloxy groups, ($C_1$–$C_6$)alkylthio groups, ($C_1$–$C_6$)alkoxycarbonyl($C_1$–$C_6$)alkoxy groups, ($C_1$–$C_6$)alkoxycarbonyl($C_1$–$C_6$)alkylthio groups, phenyl group, phenyl($C_1$–$C_6$)alkyl group, phenoxy group, phenylthio group and pyrazol-1-yl group, unsubstituted phenyl groups, ⑦ substituted phenyl groups having one or more substituents which may be the same or different and are selected from the group consisting of 2) nitro group, 3) cyano group, 5) halo($C_1$–$C_6$)alkyl groups, 6) ($C_1$–$C_6$)alkoxy groups, 7) halo($C_1$–$C_6$)alkoxy groups, 8) ($C_1$–$C_6$)alkylthio groups, 9) halo($C_1$–$C_6$)alkylthio groups, 10) ($C_2$–$C_6$)alkenyl groups, 11) ($C_2$–$C_6$)alkynyl groups, 12) ($C_1$–$C_6$)alkylcarbonyl groups, 13) carboxyl group, 14) ($C_1$–$C_{12}$)alkoxycarbonyl groups, 15) methylenedioxy group, 16) phenyl group, 17) groups represented by the formula:

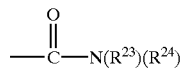

(wherein $R^{23}$ and $R^{24}$, which may be the same or different, are hydrogen atoms; ($C_1$–$C_{12}$)alkyl groups; halo($C_1$–$C_{12}$) alkyl groups; ($C_2$–$C_{12}$)alkenyl groups; ($C_2$–$C_{12}$)alkynyl groups; unsubstituted phenyl groups; substituted phenyl groups having one or more substituents which may be the same or different and are selected from the group consisting of halogen atoms, cyano group, nitro group, ($C_1$–$C_6$)alkyl groups and ($C_1$–$C_6$)alkoxy groups; or 5- or 6-membered heterocyclic rings containing, between adjacent carbon atoms of the carbon chain, one or more hetero atoms which may be the same or different and are selected from the group consisting of oxygen atom, sulfur atom and nitrogen atom), 18) groups represented by the formula:

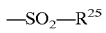

(wherein $R^{25}$ is a hydrogen atom, hydroxyl group, a ($C_1$–$C_{12}$)alkyl group, a halo($C_1$–$C_6$)alkyl group, an unsubstituted phenyl group, a substituted phenyl group having as the substituent(s) one or more substituents which may be the same or different and are selected from the group consisting of halogen atoms, ($C_1$–$C_6$)alkyl groups and ($C_1$–$C_6$)alkoxy groups, unsubstituted 1,2,3 thiadiazol-5-yl group, or substituted 1,2,3-thiadiazol-5-yl groups having halogen atom, ($C_1$–$C_6$)alkyl group or ($C_1$–$C_6$)alkoxy group as the substituent), 19) groups represented by the formula:

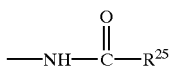

(wherein $R^{25}$ is as defined above), 20) groups represented by the formula:

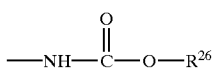

(wherein $R^{26}$ is a ($C_1$–$C_6$)alkyl group, a phenyl group or a phenyl($C_1$–$C_6$)alkyl group), 21) groups represented by the formula:

(wherein $R^{25}$ is as defined above), 22) groups represented by the formula:

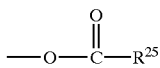

(wherein $R^{25}$ is as defined above), and 23) groups represented by the formula:

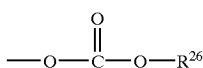

(wherein $R^{26}$ is as defined above), 24) amino group, 25) ($C_1$–$C_6$)alkylureid groups, and 26) hydroxy group, ⑳ substituted phenyl($C_1$–$C_6$)-alkyl groups having on the ring one or more substituents which may be the same or different and are selected from the group consisting of halogen atoms, nitro group, cyano group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_2$–$C_6$)alkenyl groups and ($C_2$–$C_6$)alkynyl groups, ⑳-1 phenylaminocarbonyl($C_1$–$C_6$)alkyl groups and ⑳-2 substituted phenylaminocarbonyl($C_1$–$C_6$)alkyl groups having on the ring one or more substituents which may be the same or different and are selected from the group consisting of halogen atoms, ($C_1$–$C_6$)alkyl groups and ($C_1$–$C_6$)alkoxy groups, ㉑ naphthyl groups, ㉒ groups represented by the formula:

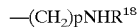

(wherein $R^{18}$ is as defined above, and p is an integer of 1 to 12), or ㉓ 5- or 6-membered heterocyclic rings having one or more hetero atoms which may be the same or different and are selected from the group consisting of oxygen atom, sulfur atom and nitrogen atom, $R^{21}$ and $R^{22}$ being able to be taken together to represent ㉔ a ($C_4$–$C_6$)alkylene group which may contain an oxygen atom between adjacent carbon atoms of the carbon chain, or ㉕ a diaminomethylene group}}, (iv) a group represented by the formula:

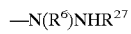

{{wherein $R^6$ is as defined above, and $R^{27}$ is ① a hydrogen atom, ② a ($C_1$–$C_{12}$)alkyl group, ③ a halo($C_1$–$C_{12}$)alkyl group, ④ a ($C_2$–$C_{12}$)alkenyl group, ⑤ a ($C_2$–$C_{12}$)alkynyl group, ⑥ a ($C_1$–$C_{12}$)alkoxy($C_1$–$C_6$)alkyl group, ⑦ a ($C_1$–$C_{12}$)alkylthio($C_1$–$C_6$)alkyl group, ⑧ a cyano($C_1$–$C_{12}$) alkyl group, ⑨ an unsubstituted phenyl group, ⑩ a substituted phenyl group having one or more substituents which may be the same or different and are selected from the group consisting of halogen atoms, nitro group, cyano group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$) alkylthio groups, halo($C_1$–$C_6$)alkylthio groups, ($C_2$–$C_6$) alkenyl groups and ($C_2$–$C_6$)alkynyl groups, ⑪ an unsubstituted phenyl($C_1$–$C_6$)alkyl group, ⑫ a substituted phenyl ($C_1$–$C_6$)alkyl group having on the ring one or more substituents which may be the same or different and are selected from the group consisting of halogen atoms, nitro group, cyano group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_2$–$C_6$)alkenyl groups and ($C_2$–$C_6$)alkynyl groups, ⑬ a group represented by the formula:

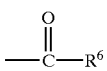

(wherein $R^6$ is as defined above), ⑭ a group represented by the formula:

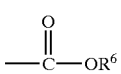

(wherein $R^6$ is as defined above), ⑮ a group represented by the formula:

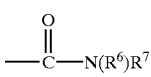

(wherein $R^6$ and $R^7$ are as defined above), or ⑯ a group represented by the formula:

(wherein $R^6$ is as defined above)}}, (v) a group represented by the formula:

{{wherein $R^6$ and $R^{27}$ are as defined above, $R^6$ and $R^{27}$ being able to be taken together to represent

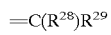

(wherein $R^{28}$ and $R^{29}$, which may be the same or different, are hydrogen atoms; $(C_1-C_6)$alkyl groups; halo$(C_1-C_6)$alkyl groups; $(C_3-C_6)$cycloalkyl groups; unsubstituted phenyl groups; substituted phenyl groups having one or more substituents which may be the same or different and are selected from the group consisting of halogen atoms, $(C_1-C_6)$alkyl groups and $(C_1-C_6)$alkoxy groups; or 5- or 6-membered heterocyclic rings containing, between adjacent carbon atoms of the carbon chain, one or more hetero atoms which may be the same or different and are selected from the group consisting of oxygen atom, sulfur atom and nitrogen atom; $R^{28}$ and $R^{29}$ being able to be taken together to represent a $(C_3-C_6)$cycloalkane ring or a 5- or 6-membered heterocyclic ring containing one or more sulfur atoms between adjacent carbon atoms of the carbon chain), or $R^6$ and $R^{27}$ being able to be taken together with the nitrogen atom to which they are bonded, to represent a 5- or 6-membered heterocyclic ring which may contain, between adjacent carbon atoms of the carbon chain, one or more hetero atoms which may be the same or different and are selected from the group consisting of oxygen atom, sulfur atom and nitrogen atom}}, or (vi) a group represented by the formula:

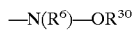

—N($R^6$)—O$R^{30}$ (wherein $R^6$ is as defined above, and $R^{30}$ is a hydrogen atom, a $(C_1-C_{12})$alkyl group, a halo$(C_1-C_{12})$alkyl group, a $(C_3-C_6)$cycloalkyl group, a $(C_2-C_{12})$alkenyl group, a $(C_2-C_{12})$alkynyl group, an unsubstituted phenyl$(C_1-C_6)$-alkyl group, or a substituted phenyl$(C_1-C_6)$alkyl group having on the ring one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_2-C_6)$alkenyl groups and $(C_2-C_6)$alkynyl groups).

2. The method of claim 1, wherein $R^1$ is ① a hydrogen atom, ② a $(C_1-C_{12})$alkyl group, ③ a halo$(C_1-C_{12})$alkyl group, ④ a $(C_2-C_{12})$alkenyl group, ⑤ a halo$(C_2-C_{12})$alkenyl group, ⑥ a $(C_2-C_{12})$alkynyl group, ⑦ a halo$(C_2-C_{12})$alkynyl group, ⑧ a $(C_3-C_6)$cycloalkyl group, ⑨ an unsubstituted phenyl group, ⑩ a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo $(C_1-C_6)$alkylthio groups, $(C_2-C_6)$alkenyl groups and $(C_2-C_6)$alkynyl groups, ⑪ a group represented by the formula:

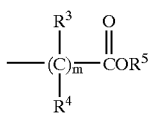

(wherein $R^3$ and $R^4$, which may be the same or different, are hydrogen atoms, $(C_1-C_{12})$alkyl groups or halo$(C_1-C_{12})$alkyl groups, m is zero or an integer of 1 to 6, and $R^5$ is a hydrogen atom; a $(C_1-C_{12})$alkyl group; a halo$(C_1-C_{12})$alkyl group; a $(C_2-C_{12})$alkenyl group; a $(C_2-C_{12})$alkynyl group; an unsubstituted phenyl group; a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo $(C_1-C_6)$alkylthio groups, $(C_2-C_6)$alkenyl groups and $(C_2-C_6)$alkynyl groups; an unsubstituted phenyl$(C_1-C_6)$alkyl group; or a substituted phenyl$(C_1-C_6)$alkyl group having on the ring one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups), ⑫ a group represented by the formula:

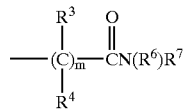

(wherein $R^3$, $R^4$ and m are as defined above, and $R^6$ and $R^7$, which may be the same or different, are hydrogen atoms; $(C_1-C_{12})$alkyl groups; halo$(C_1-C_{12})$alkyl groups; $(C_2-C_{12})$alkenyl groups; $(C_2-C_{12})$alkynyl groups; $(C_1-C_{12})$alkoxy $(C_1-C_6)$alkyl groups; $(C_1-C_{12})$alkylthio-$(C_1-C_6)$alkyl groups; cyano$(C_1-C_{12})$alkyl groups; unsubstituted phenyl groups; substituted phenyl groups having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups; unsubstituted phenyl$(C_1-C_6)$alkyl groups; or substituted phenyl $(C_1-C_6)$alkyl groups having on the ring one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups; $R^6$ and $R^7$ being able to be taken together to represent a $(C_4-C_6)$ alkylene group which may contain an oxygen atom between adjacent carbon atoms of the carbon chain), ⑬ a group represented by the formula:

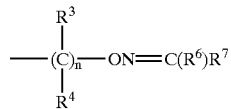

(wherein $R^3$, $R^4$, $R^6$ and $R^7$ are as defined above, and n is an integer of 1 to 6), or ⑭ a group represented by the formula:

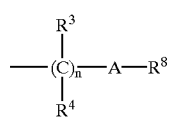

[wherein $R^3$, $R^4$ and n are as defined above, A is

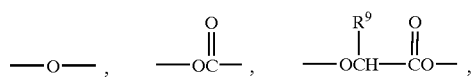

(wherein $R^9$ is a hydrogen atom, a $(C_1-C_{12})$alkyl group or a halo$(C_1-C_{12})$alkyl group),

—S—,
—SO—,
—SO$_2$—,

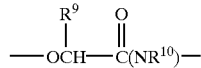

{wherein $R^9$ is as defined above, and $R^{10}$ is a hydrogen atom, a $(C_1-C_{12})$alkyl group or a halo$(C_1-C_{12})$alkyl group, $R^9$ and $R^{10}$ being able to be taken together to represent a $(C_4-C_6)$alkylene group which may contain, between adjacent carbon atoms of the carbon chain, an oxygen atom, a sulfur atom or

N—$R^{11}$ (wherein $R^{11}$ is a hydrogen atom, a $(C_1-C_{12})$alkyl group or a halo$(C_1-C_{12})$alkyl group)}, or

—N($R^{10}$)—

(wherein $R^{10}$ is as defined above), and $R^8$ is a hydrogen atom; a $(C_1-C_{12})$alkyl group; a halo$(C_1-C_{12})$alkyl group; a $(C_2-C_{12})$alkenyl group; a $(C_2-C_{12})$alkynyl group; a $(C_1-C_{12})$alkoxy$(C_1-C_{12})$alkyl group; a $(C_1-C_{12})$alkylthio-$(C_1-C_{12})$alkyl group; a cyano $(C_1-C_{12})$alkyl group; an unsubstituted phenyl group; a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups; an unsubstituted phenyl$(C_1-C_6)$alkyl group; a substituted phenyl$(C_1-C_6)$alkyl group having on the ring one or more substituents which may be the same or different and are selected from the group consisting of halogen atoms, nitro group, cyano group, $(C_1-C_6)$alkyl groups, halo$(C_1-C_6)$ alkyl groups, $(C_1-C_6)$alkoxy groups, halo$(C_1-C_6)$ alkoxy groups, $(C_1-C_6)$alkylthio groups, halo$(C_1-C_6)$ alkylthio groups, $(C_2-C_6)$alkenyl groups and $(C_2-C_6)$ alkynyl groups; an unsubstituted 5- or 6-membered heterocyclic ring having one or more heteroatoms which may be the same or different and are selected from the group consisting of oxygen atom, sulfur atom and nitrogen atom; or a substituted 5- or 6-membered heterocyclic ring having one or more heteroatoms which may be the same or different and are selected from the group consisting of oxygen atom, sulfur atom and nitrogen atom, said substituted heterocyclic ring having one or more substituents which may be the same or different and are selected from the group consisting of halogen atoms, nitro group, cyano group, $(C_1-C_6)$ alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups], and $R^2$ is (i) a group represented by the formula:

—X—$R^{12}$

[wherein X is an oxygen atom or a sulfur atom, and $R^{12}$ is ① a hydrogen atom, ② $(C_1-C_{12})$alkyl group, ③ a halo$(C_1-C_{12})$alkyl group, ④ a $(C_2-C_{20})$alkenyl group, ⑤ a halo$(C_2-C_{20})$alkenyl group, ⑥ a $(C_2-C_{12})$ alkynyl group, ⑦ a halo$(C_2-C_{12})$alkynyl group, ⑧ a hydroxy$(C_1-C_6)$alkyl group, ⑨ a $(C_1-C_{12})$alkoxy $(C_1-C_{12})$alkyl group, ⑩ a $(C_1-C_{12})$alkylthio$(C_1-C_{12})$ alkyl group, ⑪ a $(C_3-C_6)$cycloalkyl group, ⑫ a $(C_3-C_6)$cycloalkyl$(C_1-C_{12})$alkyl group, ⑬ an unsubstituted phenyl group, ⑭ a substituted phenyl group having one more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups, $(C_2-C_6)$alkynyl groups and $(C_1-C_6)$alkoxycarbonyl$(C_1-C_6)$alkyloxy groups, ⑮ an unsubstituted phenyl$(C_1-C_6)$alkyl group, ⑯ a substituted phenyl $(C_1-C_6)$alkyl group having on the ring one or more substituents which may be the same or different and are selected from the group consisting of halogen atoms, nitro group, cyano group, $(C_1-C_6)$alkyl groups, halo $(C_1-C_6)$alkyl groups, $(C_1-C_6)$alkoxy groups, halo $(C_1-C_6)$alkoxy groups, $(C_1-C_6)$alkylthio groups, halo $(C_1-C_6)$alkylthio groups, $(C_2-C_6)$alkenyl groups and $(C_2-C_6)$alkynyl groups, ⑰ a diphenyl$(C_1-C_6)$alkyl group, ⑱ a phenoxy$(C_1-C_6)$alkyl group, ⑲ a group represented by the formula:

—B—N($R^{13}$)$R^{14}$

{wherein B is a $(C_1-C_6)$alkylene group which may be substituted by a $(C_1-C_6)$alkyl group or a phenyl group, and $R^{13}$ and $R^{14}$, which may be the same or different, are hydrogen atoms; formyl groups; $(C_1-C_{12})$alkyl groups; $(C_2-C_{12})$alkenyl groups; $(C_2-C_{12})$alkynyl groups; alkylcarbonyl groups; unsubstituted phenyl groups; substituted phenyl groups having one or more substituents which may be the same or different and are selected from the group consisting of hydrogen atom, halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups; phenylcarbonyl groups; unsubstituted 1,2,3-thiadiazol-5-yl-carbonyl groups; or substituted 1,2,3-thiadiazol-5-yl-carbonyl groups having a halogen atom or a $(C_1-C_6)$alkyl group as the substituent; $R^{13}$ and $R^{14}$ being able to be taken together to represent a $(C_4-C_5)$alkylene group which may contain, between adjacent carbon atoms of the carbon chain, an oxygen atom, a sulfur atom or

N—$R^{11}$ (wherein $R^{11}$ is as defined above)}, ⑳ a group represented by the formula:

—C($R^{15}$)=C($R^{16}$)—$R^{17}$ (wherein $R^{15}$ is a hydrogen atom or a $(C_1-C_6)$alkyl group, $R^{16}$ is a hydrogen atom, a halogen atom or a $(C_1-C_6)$alkyl group, and $R^{17}$ is a nitro group, a cyano group, a $(C_1-C_6)$alkylcarbonyl group, a $(C_1-C_6)$ alkoxycarbonyl group, a phenylcarbonyl group, or a substituted aminocarbonyl group having one or more substituents which may be the same or different and are selected from the group consisting of hydrogen atom, $(C_1-C_{12})$alkyl groups, unsubstituted phenyl group, and substituted phenyl groups having one or more substituents which may be the same or different and are selected from the group consisting of halogen atoms, cyano group, nitro group, $(C_1-C_6)$alkyl groups and $(C_1-C_6)$alkoxy groups, $R^{15}$ and $R^{17}$ being able to be taken together to represent a $(C_3-C_6)$alkylene group which may be substituted by one or more $(C_1-C_6)$alkyl group and/or an oxo group), ㉑ a group represented by the formula:

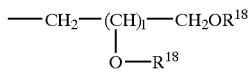

(wherein two $R^{18}$'s, which may be the same or different, are hydrogen atoms, $(C_1-C_6)$alkylcarbonyl groups, phenylcarbonyl groups, unsubstituted 1,2,3-thiadiazol-5-yl-carbonyl groups, or substituted 1,2,3-thiadiazol-5-yl-carbonyl groups having a halogen atom or a $(C_1-C_6)$alkyl group as the substituent, and l is zero or an integer of 1 to 12), or ㉒ a 5- or 6-membered heterocyclic alkyl group having one or more heteroatoms which may be the same or different and are selected from the group consisting of oxygen atom, sulfur atom and nitrogen atom, ㉓ a tri$(C_1-C_6)$alkylsilyl$(C_1-C_6)$alkyl groups, or ㉔ 1,2,3-thiadiazol-5-yl-carbonyloxy-$(C_1-C_{12})$alkyl groups having on the ring a halogen atom or $(C_1-C_6)$alkyl group as the substituent].

3. The method for controlling agricultural and horticultural diseases of plants according to claim 1, wherein $R^1$ is ① a hydrogen atom, ② a $(C_1-C_{12})$alkyl group, ③ a halo$(C_1-C_6)$alkyl group, ④ a $(C_2-C_{12})$alkenyl group, ⑤ a halo$(C_2-C_{12})$alkenyl group, ⑥ a $(C_2-C_{12})$alkynyl group, ⑦ a halo$(C_2-C_{12})$alkynyl group, ⑧ a $(C_3-C_6)$cycloalkyl group, ⑨ an unsubstituted phenyl group, ⑩ a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups, ⑪ a group represented by the formula:

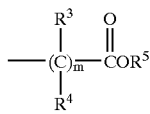

(wherein $R^3$ and $R^4$, which may be the same or different, are hydrogen atoms, $(C_1-C_{12})$alkyl groups or halo$(C_1-C_{12})$alkyl groups, m is zero or an integer of 1 to 6, and $R^5$ is a hydrogen atom; a $(C_1-C_{12})$alkyl group; a halo$(C_1-C_{12})$alkyl group; a $(C_2-C_{12})$alkenyl group; a $(C_2-C_{12})$alkynyl group; an unsubstituted phenyl group; a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, halo$(C_1-C_6)$alkylthio groups, $(C_2-C_6)$alkenyl groups and $(C_2-C_6)$alkynyl groups; an unsubstituted phenyl$(C_1-C_6)$alkyl group; or a substituted phenyl$(C_1-C_6)$alkyl group having on the ring one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups), ⑫ a group represented by the formula:

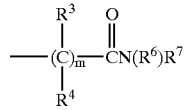

(wherein $R^3$, $R^4$ and m are as defined above, and $R^6$ and $R^7$, which may be the same or different, are hydrogen atoms; $(C_1-C_{12})$alkyl groups; halo$(C_1-C_{12})$alkyl groups; $(C_2-C_{12})$alkenyl groups; $(C_2-C_{12})$alkynyl groups; $(C_1-C_{12})$alkoxy $(C_1-C_6)$alkyl groups; $(C_1-C_{12})$alkylthio-$(C_1-C_6)$alkyl groups; cyano$(C_1-C_{12})$alkyl groups; unsubstituted phenyl groups; substituted phenyl groups having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2C_6)$alkynyl groups; unsubstituted phenyl$(C_1-C_6)$alkyl groups; or substituted phenyl $(C_1-C_6)$alkyl groups having on the ring one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups; $R^6$ and $R^7$ being able to be taken together to represent a $(C_4-C_6)$alkylene group which may contain an oxygen atom between adjacent carbon atoms of the carbon chain), ⑬ a group represented by the formula:

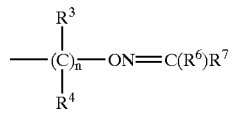

(wherein $R^3$, $R^4$, $R^6$ and $R^7$ are as defined above, and n is an integer of 1 to 6), or ⑭ a group represented by the formula:

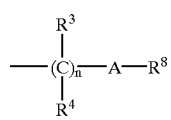

{{wherein $R^3$, $R^4$ and n are as defined above, A is

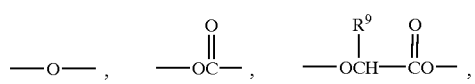

(wherein $R^9$ is a hydrogen atom, a $(C_1-C_{12})$alkyl group or a halo$(C_1-C_{12})$alkyl group),

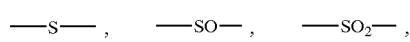

-continued

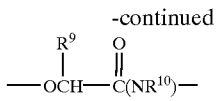

{{wherein $R^9$ is as defined above, and $R^{10}$ is a hydrogen atom, a $(C_1-C_{12})$alkyl group or a halo$(C_1-C_{12})$alkyl group, $R^9$ and $R^{10}$ being able to be taken together to represent a $(C_4-C_6)$alkylene group which may contain, between adjacent carbon atoms of the carbon chain, an oxygen atom, a sulfur atom or

(wherein $R^{11}$ is a hydrogen atom, a $(C_1-C_{12})$alkyl group or a halo$(C_1-C_{12})$alkyl group), or

(wherein $R^{10}$ is as defined above), and $R^8$ is a hydrogen atom; a $(C_1-C_{12})$alkyl group; a halo$(C_1-C_{12})$alkyl group; a $(C_2-C_{12})$alkenyl group; a $(C_2-C_{12})$alkynyl group; a $(C_1-C_{12})$alkoxy$(C_1-C_{12})$alkyl group; a $(C_1-C_{12})$alkylthio-$(C_1-C_{12})$alkyl group; a cyano$(C_1-C_{12})$alkyl group; an unsubstituted phenyl group; a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups; an unsubstituted phenyl$(C_1-C_6)$-alkyl group; a substituted phenyl$(C_1-C_6)$alkyl group having on the ring one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkyl-thio groups, halo$(C_1-C_6)$alkylthio groups, $(C_2-C_6)$alkenyl groups and $(C_2-C_6)$alkynyl groups; an unsubstituted 5- or 6-membered heterocyclic ring having one or more heteroatoms which may be the same or different and are selected from the group consisting of oxygen atom, sulfur atom and nitrogen atom; or a substituted 5- or 6-membered heterocyclic ring having one or more heteroatoms which may be the same or different and are selected from the group consisting of oxygen atom, sulfur atom and nitrogen atom, said substituted heterocyclic ring having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$ alkoxy groups, halo$(C_1-C_6)$alkoxy groups, $(C_1-C_6)$alkyl-thio groups, halo$(C_1-C_6)$alkylthio groups, $(C_2-C_6)$alkenyl groups and $(C_2-C_6)$alkynyl groups}}, and $R^2$ is (iii) a group represented by the formula:

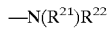

{{wherein $R^{21}$ and $R^{22}$, which may be the same or different, are ② $(C_1-C_{12})$alkyl groups, ③ unsubstituted halo$(C_1-C_{12})$alkyl groups, ④ substituted halo$(C_1-C_{12})$alkyl groups having a hydroxyl group or a $(C_1-C_6)$alkoxy group as the substituent, ⑤ $(C_2-C_{12})$alkenyl groups, ⑥ $(C_2-C_{12})$alkynyl groups, ⑦ $(C_1-C_{12})$alkoxy$(C_1-C_6)$alkyl groups, ⑧ $(C_1-C_{12})$alkylthio$(C_1-C_6)$alkyl groups, ⑨ cyano$(C_1-C_{12})$alkyl groups, ⑩ substituted cyano$(C_1-C_6)$alkyl groups having on the alkyl chain a substituent selected from the group consisting of $(C_1-C_6)$alkoxy groups, $(C_2-C_6)$ alkenyloxy groups, $(C_2-C_6)$alkynyloxy groups, $(C_1-C_6)$ alkylthio groups, $(C_1-C_6)$alkoxycarbonyl$(C_1-C_6)$alkoxy groups, $(C_1-C_6)$alkoxycarbonyl$(C_1-C_6)$alkylthio groups, phenoxy group, phenylthio group and pyrazol-1-yl group, ⑪ unsubstituted carbamoyl$(C_1-C_6)$alkyl groups, ⑫ substituted carbamoyl$(C_1-C_6)$alkyl groups having on the alkyl chain a substituent selected from the group consisting of $(C_1-C_6)$alkoxy groups, $(C_2-C_6)$alkenyloxy groups, $(C_2-C_6)$ alkynyloxy groups, $(C_1-C_6)$alkylthio groups, $(C_1-C_6)$ alkoxycarbonyl$(C_1-C_6)$alkoxy groups, $(C_1-C_6)$ alkoxycarbonyl$(C_1-C_6)$alkylthio groups, phenoxy group, phenylthio group and pyrazol-14-yl group, ⑬ hydroxy$(C_1-C_6)$alkyl groups, ⑭ di$(C_1-C_6)$alkoxy$(C_1-C_6)$alkyl groups in which the $(C_1-C_6)$alkoxy groups may be the same or different, ⑮ unsubstituted $(C_1-C_6)$alkoxycarbonyl-$(C_1-C_6)$alkyl groups, ⑯ substituted $(C_1-C_6)$alkoxycarbonyl$(C_1-C_6)$alkyl groups having on the alkyl chain a substituent selected from the group consisting of $(C_1-C_6)$ alkyl groups, $(C_1-C_6)$alkoxy groups, $(C_2-C_6)$alkenyloxy groups, $(C_2-C_6)$alkynyloxy groups, $(C_1-C_6)$alkylthio groups, $(C_1-C_6)$alkoxycarbonyl$(C_1-C_6)$alkoxy groups, $(C_1-C_6)$alkoxycarbonyl$(C_1-C_6)$alkylthio groups, phenyl group, phenyl$(C_1-C_6)$alkyl group, phenoxy group, phenylthio group and pyrazol-1-yl group, ⑰ unsubstituted phenyl groups, ⑱ substituted phenyl groups having one or more substituents which may be the same or different and are selected from the group consisting of 2) nitro group, 3) cyano group, 5) halo$(C_1-C_6)$alkyl groups, 6) $(C_1-C_6)$alkoxy groups, 7) halo$(C_1-C_6)$alkoxy groups, 8) $(C_1-C_6)$alkylthio groups, 9) halo$(C_1-C_6)$alkyl-thio groups, 10) $(C_2-C_6)$alkenyl groups, 11) $(C_2-C_6)$alkynyl groups, 12) $(C_1-C_6)$ alkylcarbonyl groups, 13) carboxyl group, 14) $(C_1-C_{12})$ alkoxycarbonyl groups, 15) methylenedioxy group, 16) phenyl group, 17) groups represented by the formula:

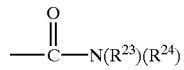

(wherein $R^{23}$ and $R^{24}$, which may be the same or different, are hydrogen atoms; $(C_1-C_{12})$alkyl groups; halo$(C_1-C_{12})$ alkyl groups; $(C_2-C_{12})$alkenyl groups; $(C_2-C_{12})$alkynyl groups; unsubstituted phenyl groups; substituted phenyl groups having one or more substituents which may be the same or different and are selected from the group consisting of halogen atoms, cyano group, nitro group, $(C_1-C_6)$alkyl groups and $(C_1-C_6)$alkoxy groups; or 5- or 6-membered heterocyclic rings containing, between adjacent carbon atoms of the carbon chain, one or more atoms which may be the same or different and are selected from the group consisting of oxygen atom, sulfur atom and nitrogen atom), 18) groups represented by the formula:

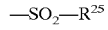

(wherein $R^{25}$ is a hydrogen atom, hydroxyl group, a $(C_1-C_{12})$alkyl group, a halo$(C_1-C_6)$alkyl group, an unsubstituted phenyl group, a substituted phenyl group having as the substituent(s) one or more substituents which may be the same or different and are selected from the group consisting of halogen atoms, $(C_1-C_6)$alkyl groups and $(C_1-C_6)$alkoxy groups, unsubstituted 1,2,3 thiadiazol-5-yl group, or substituted 1,2,3-thiadiazol-5-yl groups having halogen atom, $(C_1-C_6)$alkyl group or $(C_1-C_6)$alkoxy group as the substituent), 19) groups represented by the formula:

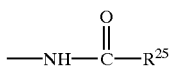

(wherein $R^{25}$ is as defined above), 20) groups represented by the formula:

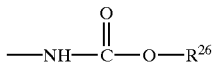

(wherein $R^{26}$ is a $(C_1-C_6)$alkyl group, a phenyl group or a phenyl$(C_1-C_6)$alkyl group, 21) groups represented by the formula:

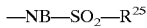

(wherein $R^{25}$ is as defined above), 22) groups represented by the formula:

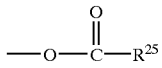

(wherein $R^{25}$ is as defined above), and 23) groups represented by the formula:

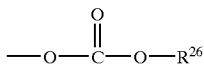

(wherein $R^{26}$ is as defined above), ⑳ substituted phenyl $(C_1-C_6)$alkyl groups having on the ring one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups, ㉑ naphthyl groups, ㉒ groups represented by the formula:

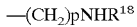

(wherein $R^{18}$ is as defined above, and p is an integer of 1 to 12), or ㉓ 5- or 6-membered heterocyclic rings having one or more hetero atoms which may be the same or different and are selected from the group consisting of oxygen atom, sulfur atom and nitrogen atom, $R^{21}$ and $R^{22}$ being able to be taken together to represent ㉔ a $(C_4-C_6)$alkylene group which may contain an oxygen atom between adjacent carbon atoms of the carbon chain, or ㉕ a diaminomethylene group}}.

4. The method of claim 2, wherein $R^1$ is ① a hydrogen atom, ② a $(C_1-C_{12})$alkyl group, ③ a halo$(C_1-C_{12})$alkyl group, ④ a $(C_2-C_{12})$alkenyl group, ⑤ a halo$(C_2-C_{12})$alkenyl group, ⑥ a $(C_2-C_{12})$alkynyl group, ⑦ a halo$(C_2-C_{12})$alkynyl group, ⑧ a $(C_3-C_6)$cycloalkyl group, ⑨ an unsubstituted phenyl group, or ⑩ a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups, and $R^2$ is (i) a group represented by the formula:

[wherein X is an oxygen atom or a sulfur atom, and $R^{12}$ is ① a hydrogen atom, ② a $(C_1-C_{12})$alkyl group, ③ a halo$(C_1-C_{12})$alkyl group, ④ a $(C_2-C_{20})$alkenyl group, ⑤ a halo$(C_2-C_{20})$alkenyl group, ⑥ a $(C_2-C_{12})$alkynyl group, ⑦ a halo$(C_2-C_{12})$alkynyl group, ⑧ a hydroxy$(C_1-C_6)$alkyl group, ⑨ a $(C_1-C_{12})$alkoxy$(C_1-C_{12})$alkyl group, ⑪ a $(C_3-C_6)$cycloalkyl group, ⑬ an unsubstituted phenyl group, ⑭ a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, and $(C_1-C_6)$alkoxycarbonyl-$(C_1-C_6)$alkyloxy groups, ⑮ an unsubstituted phenyl$(C_1-C_6)$alkyl group, ⑯ a substituted phenyl$(C_1-C_6)$alkyl group having on the ring one or more substituents which may be the same or different and are selected from the group consisting of halogen atoms, nitro group, cyano group, $(C_1-C_6)$alkyl groups, halo$(C_1-C_6)$ alkyl groups, $(C_1-C_6)$alkoxy groups, and halo$(C_1-C_6)$ alkoxy groups, ⑰ a diphenyl$(C_1-C_6)$alkyl group, ⑱ a phenoxy$(C_1-C_6)$alkyl group, ⑲ a group represented by the formula:

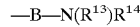

{wherein B is a $(C_1-C_6)$alkylene group which may be substituted by a $(C_1-C_6)$alkyl group or a phenyl group, and $R^{13}$ and $R^{14}$, which may be the same or different, are hydrogen atoms; formyl groups; $(C_1-C_{12})$alkyl groups; $(C_2-C_{12})$alkenyl groups; $(C_2-C_{12})$alkynyl groups; $(C_1-C_{12})$alkylcarbonyl groups; unsubstituted phenyl groups; substituted phenyl groups having one or more substituents which may be the same or different and are selected from the group consisting of hydrogen atom, halogen atoms, nitro group, cyano group, $(C_1-C_6)$alkyl groups, halo$(C_1-C_6)$alkyl groups, $(C_1-C_6)$alkoxy groups, and halo$(C_1-C_6)$alkoxy groups; phenylcarbonyl groups; unsubstituted 1,2,3-thiadiazol-5-yl-carbonyl groups; or substituted 1,2,3-thiadiazol-5-yl-carbonyl groups having a halogen atom or a $(C_1-C_6)$alkyl group as the substituent; ㉑ a group represented by the formula:

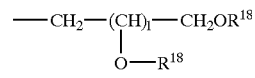

(wherein two $R^{18}$'s, which may be the same or different, are hydrogen atoms, $(C_1-C_6)$alkylcarbonyl groups, phenylcarbonyl groups, unsubstituted 1,2,3-thiadiazol-5-yl-carbonyl groups, or substituted 1,2,3-thiadiazol-5-yl-carbonyl groups having a halogen atom or a $(C_1-C_6)$alkyl group as the substituent, and l is zero or an integer of 1 to 12), or (1,2,3-thiadiazol-5-yl-carbonyloxy$(C_1-C_6)$alkyl groups having on the ring a halogen atom or $(C_1-C_6)$alkyl group as the substituent].

5. The method of claim 1, wherein $R^1$ is ① a hydrogen atom, ② a $(C_1-C_{12})$alkyl group, ③ a halo$(C_1-C_{12})$alkyl group, ④ a $(C_2-C_{12})$alkenyl group, ⑤ a halo$(C_2-C_{12})$ alkenyl group, ⑥ a $(C_2-C_{12})$alkynyl group, ⑦ a halo $(C_2-C_{12})$alkynyl group, ⑧ a $(C_3-C_6)$cycloalkyl group, ⑨ an unsubstituted phenyl group, or ⑩ a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo $(C_1-C_6)$alkylthio groups, $(C_2-C_6)$alkenyl groups and ($C_2$–$C_6$)alkynyl groups, and $R^2$ is (ii) a group represented by the formula:

$$-O-N=C(R^{19})R^{20}$$

[wherein $R^{19}$ and $R^{20}$, which may be the same or different, are ① hydrogen atoms, ② halogen atoms, ④ cyano groups, ⑤ ($C_1$–$C_{12}$)alkyl groups, ⑥ halo($C_1$–$C_{12}$)alkyl groups, ⑦ ($C_3$–$C_6$)cycloalkyl groups, ⑧ ($C_2$–$C_{12}$)alkenyl groups, ⑨ ($C_2$–$C_{12}$)alkynyl groups, ⑩ ($C_1$–$C_{12}$)alkoxy ($C_1$–$C_{12}$)alkyl groups, ⑪ ($C_1$–$C_{12}$)alkoxycarbonyl groups, ⑫ unsubstituted phenyl groups, ⑬ substituted phenyl groups having one or more substituents which may be the same or different and are selected from the group consisting of halogen atoms, nitro group, cyano group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo ($C_1$–$C_6$)alkylthio groups, ($C_2$–$C_6$)alkenyl groups and ($C_2$–$C_6$)alkynyl groups, ⑭ unsubstituted 5- or 6-membered heterocyclic rings having one or more heteroatoms which may be the same or different and are selected from the group consisting of oxygen atom, sulfur atom and nitrogen atom, ⑮ substituted 5- or 6-membered heterocyclic rings having one or more heteroatoms which may be the same or different and are selected from the group consisting of oxygen atom, sulfur atom and nitrogen atom, said substituted heterocyclic ring having one or more substituents which may be the same or different and are selected from the group consisting of halogen atoms, nitro group, cyano group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_2$–$C_6$)alkenyl groups and ($C_2$–$C_6$)alkynyl groups, ⑯ groups represented by the formula;

$$-SR^5$$

(wherein $R^5$ is as defined above), ⑰ groups represented by the formula:

$$-N(R^6)R^7$$

(wherein $R^6$ and $R^7$ are as defined above), $R^{19}$ and $R^{20}$ being able to be taken together to represent ⑱ a ($C_3$–$C_6$) cycloalkane ring or ⑲ a 5- or 6-membered heterocyclic ring containing, between adjacent carbon atoms of the carbon chain, one or more hetero atoms which may be the same or different and are selected from the group consisting of oxygen atom, sulfur atom and nitrogen atom].

6. The method of controlling agricultural and horticultural diseases of plants according to claim 4, wherein $R^1$ is ① a hydrogen atom, ② a ($C_1$–$C_{12}$)alkyl group, ③ a halo ($C_1$–$C_{12}$)alkyl group, ④ a ($C_2$–$C_{12}$)alkenyl group, ⑤ a halo($C_1$–$C_{12}$)alkenyl group, ⑥ a ($C_2$–$C_{12}$)alkynyl group, ⑦ a halo($C_2$–$C_{12}$)alkynyl group, ⑧ a ($C_3$–$C_6$)cycloalkyl group, ⑨ an unsubstituted phenyl group, or ⑩ a substituted phenyl group having one or more substituents which may be the same or different and are selected from the group consisting of halogen atoms, nitro group, cyano group, ($C_1$–$C_6$)alkyl groups, halo($C_1$–$C_6$)alkyl groups, ($C_1$–$C_6$) alkoxy groups, halo($C_1$–$C_6$)alkoxy groups, ($C_1$–$C_6$) alkylthio groups, halo($C_1$–$C_6$)alkylthio groups, ($C_2$–$C_6$) alkenyl groups and ($C_2$–$C_6$)alkynyl groups, and $R^2$ is (iii) a group represented by the formula:

$$-N(R^{21})R^{22}$$

{{wherein $R^{21}$ and $R^{22}$, which may be the same or different, are ② ($C_1$–$C_{12}$)alkyl groups, ③ unsubstituted halo ($C_1$–$C_{12}$)alkyl groups, ⑤ ($C_2$–$C_{12}$)alkenyl groups, ⑥ ($C_2$–$C_{12}$)alkynyl groups, ⑦ ($C_1$–$C_{12}$)alkoxy($C_1$–$C_6$)alkyl groups, ⑧ ($C_1$–$C_{12}$)alkylthio-($C_1$–$C_6$)alkyl groups, ⑨ cyano($C_1$–$C_{12}$)alkyl groups, ⑪ unsubstituted carbamoyl ($C_1$–$C_6$)alkyl groups, ⑬ hydroxy ($C_1$–$C_6$)alkyl groups, ⑮ unsubstituted ($C_1$–$C_6$)alkoxy-carbonyl($C_1$–$C_6$)alkyl groups, ⑰ unsubstituted phenyl groups, ⑱ substituted phenyl groups having one or more substituents which may be the same or different and are selected from the group consisting of 2) nitro group, 3) cyano group, 5) halo($C_1$–$C_6$) alkyl groups, 6) ($C_1$–$C_6$)alkoxy groups, 7) halo($C_1$–$C_6$) alkoxy groups, 8) ($C_1$–$C_6$)alkylthio groups, 12) ($C_1$–$C_6$) alkylcarbonyl groups, 13) carboxyl group, 14) ($C_1$–$C_{12}$) alkoxycarbonyl groups, 15) methylenedioxy group, 16) phenyl group, 17) groups represented by the formula:

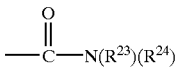

(wherein $R^{23}$ and $R^{24}$, which may be the same or different, are hydrogen atoms; ($C_1$–$C_{12}$)alkyl groups; halo($C_1$–$C_{12}$) alkyl groups; ($C_2$–$C_{12}$)alkenyl groups; ($C_2$–$C_{12}$)alkynyl groups; unsubstituted phenyl groups; substituted phenyl groups having one or more substituents which may be the same or different and are selected from the group consisting of halogen atoms, cyano group, nitro group, ($C_1$–$C_6$)alkyl groups and ($C_1$–$C_6$)alkoxy groups; or 5- or 6-membered heterocyclic rings containing, between adjacent carbon atoms of the carbon chain, one or more atoms which may be the same or different and are selected from the group consisting of oxygen atom, sulfur atom and nitrogen atom), 18) groups represented by the formula: $-SO_2-R^{25}$ (wherein $R^{25}$ is a hydrogen atom, hydroxyl group, a ($C_1$–$C_6$) alkyl group, a halo($C_1$–$C_6$)alkyl group, an unsubstituted phenyl group, a substituted phenyl group having as the substituent(s) one or more substituents which may be the same or different and are selected from the group consisting of halogen atoms, ($C_1$–$C_6$)alkyl groups and ($C_1$–$C_6$)alkoxy groups, unsubstituted 1,2,3thiadiazol-5-yl group, or substituted 1,2,3-thiadiazol-5-yl groups having halogen atom, ($C_1$–$C_6$)alkyl group or ($C_1$–$C_6$)alkoxy group as the substituent), 19) groups represented, by the formula:

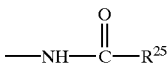

(wherein $R^{25}$ is as defined above), 20) groups represented by the formula:

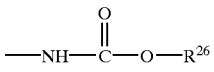

(wherein $R^{26}$ is a ($C_1$–$C_6$)alkyl group, a phenyl group or a phenyl($C_1$–$C_6$)alkyl group), 21) groups represented by the formula:

(wherein $R^{25}$ is as defined above), 22) groups represented by the formula:

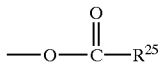

(wherein $R^{25}$ is as defined above), and 23) groups represented by the formula:

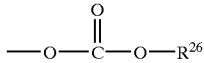

(wherein $R^{26}$ is as defined above), ⑳ substituted phenyl ($C_1$–$C_6$)-alkyl groups having on the ring one or more substituents which may be the same or different and are selected from the group consisting of halogen atoms, nitro group, cyano group, ($C_1$–$C_6$)alkyl groups, halo($C_1$–$C_6$)alkyl groups, ($C_1$–$C_6$)alkoxy groups, and halo($C_1$–$C_6$)alkoxy groups, ㉑ naphthyl groups, ㉒ groups represented by the formula:

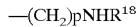

—(CH$_2$)pNHR$^{18}$ (wherein $R^{18}$ is as defined above, and p is an integer of 1 to 12), or ㉓ 5- or 6-membered heterocyclic rings having one or more atoms which may be the same or different and are selected from the group consisting of oxygen atom, sulfur atom and nitrogen atom, $R^{21}$ and $R^{22}$ being able to be taken together to represent ㉔ a ($C_4$–$C_6$)alkylene group which may contain an oxygen atom between adjacent carbon atoms of the carbon chain, or a diaminomethylene group}}.

7. The method of claim 1, wherein $R^1$ is ① a hydrogen atom, ② a ($C_1$–$C_{12}$)alkyl group, ③ a halo($C_1$–$C_{12}$)alkyl group, ④ a ($C_2$–$C_{12}$)alkenyl group, ⑤ a halo($C_2$–$C_{12}$)alkenyl group, ⑥ a ($C_2$–$C_{12}$)alkynyl group, ⑦ a halo($C_2$–$C_{12}$)alkynyl group, ⑧ a ($C_3$–$C_6$)cycloalkyl group, ⑨ an unsubstituted phenyl group, or ⑩ a substituted phenyl group having one or more substituents which may be the same or different and are selected from the group consisting of halogen atoms, nitro group, cyano group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_2$–$C_6$)alkenyl groups and ($C_2$–$C_6$)alkynyl groups, and $R^2$ is (iv) a group represented by the formula:

—N(R$^6$)NHR$^{27}$

[wherein $R^6$ is as defined above, and $R^{27}$ is ① a hydrogen atom, ① a ($C_1$–$C_{12}$)alkyl group, ③ a halo($C_1$–$C_{12}$)alkyl group, ④ a ($C_2$–$C_{12}$)alkenyl group, ⑤ a ($C_2$–$C_{12}$)alkynyl group, ⑧ a cyano($C_1$–$C_{12}$)alkyl group, ⑨ an unsubstituted phenyl group, ⑩ a substituted phenyl group having one or more substituents which may be the same or different and are selected from the group consisting of halogen atoms, nitro group, cyano group, ($C_1$–$C_6$)alkyl groups, halo($C_1$–$C_6$) alkyl groups, ($C_1$–$C_6$)alkoxy groups, and halo($C_1$–$C_6$) alkoxy groups, ⑪ an unsubstituted phenyl($C_1$–$C_6$)alkyl group, ⑫ a substituted phenyl($C_1$–$C_6$)alkyl group having on the ring one or more substituents which may be the same or different and are selected from the group consisting of halogen atoms, nitro group, cyano group, ($C_1$–$C_6$)alkyl groups, halo($C_1$–$C_6$)alkyl groups, ($C_1$–$C_6$)alkoxy groups and halo($C_1$–$C_6$)alkoxy groups, ⑬ a group represented by the formula:

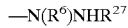

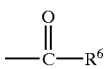

(wherein $R^6$ is as defined above), ⑭ a group represented by the formula:

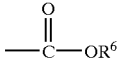

(wherein $R^6$ is as defined above), ⑮ a group represented by the formula:

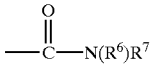

(wherein $R^6$ and $R^7$ are as defined above), or ⑯ a group represented by the formula:

—SO$_2$—R$^6$ (wherein $R^6$ is as defined above)].

8. The method of claim 1, wherein $R^1$ is ① a hydrogen atom, ② a ($C_1$–$C_{12}$)alkyl group, ③ a halo($C_1$–$C_{12}$)alkyl group, ④ a ($C_2$–$C_{12}$)alkenyl group, ⑤ a halo($C_2$–$C_{12}$)alkenyl group, ⑥ a ($C_2$–$C_{12}$)alkynyl group, ⑦ a halo($C_2$–$C_{12}$)alkynyl group, ⑧ a ($C_3$–$C_6$)cycloalkyl group, ⑨ an unsubstituted phenyl group, or ⑩ a substituted phenyl group having one or more substituents which may be the same or different and are selected from the group consisting of halogen atoms, nitro group, cyano group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_2$–$C_6$)alkenyl groups and ($C_2$–$C_6$)alkynyl groups, and $R^2$ is (v) a group represented by the formula:

—NHN(R$^6$)R$^{27}$

[wherein $R^6$ is as defined above and $R^{27}$ is ① a hydrogen atom, ① a ($C_1$–$C_{12}$)alkyl group, ③ a halo($C_1$–$C_{12}$)alkyl group, ④ a ($C_2$–$C_{12}$)alkenyl group, ⑤ a ($C_2$–$C_{12}$)alkynyl group, ⑧ a cyano($C_1$–$C_{12}$)alkyl group, ⑨ an unsubstituted phenyl group, ⑩ a substituted phenyl group having one or more substituents which may be the same or different and are selected from the group consisting of halogen atoms, nitro group, cyano group, ($C_1$–$C_6$)alkyl groups, halo($C_1$–$C_6$) alkyl groups, ($C_1$–$C_6$)alkoxy groups, and halo($C_1$–$C_6$) alkoxy groups, ⑪ an unsubstituted phenyl($C_1$–$C_6$)alkyl group, ⑫ a substituted phenyl($C_1$–$C_6$)alkyl group having on the ring one or more substituents which may be the same or different and are selected from the group consisting of halogen atoms, nitro group, cyano group, ($C_1$–$C_6$)alkyl groups, halo($C_1$–$C_6$)alkyl groups, ($C_1$–$C_6$)alkoxy groups and halo($C_1$–$C_6$)alkoxy groups, ⑬ a group represented by the formula:

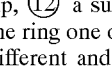

(wherein $R^6$ is as defined above), 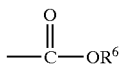 a group represented by the formula:

$$-\overset{\overset{\displaystyle O}{\|}}{C}-OR^6$$

(wherein $R^6$ is as defined above), 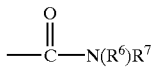 a group represented by the formula:

$$-\overset{\overset{\displaystyle O}{\|}}{C}-N(R^6)R^7$$

(wherein $R^6$ and $R^7$ are as defined above), or  a group represented by the formula:

$$-SO_2-R^6$$

(wherein $R^6$ is as defined above)], $R^6$ and $R^{27}$ being able to be taken together to represent $$=C(R^{28})R^{29}$$

(wherein $R^{28}$ and $R^{29}$, which may be the same or different, are hydrogen atoms; $(C_1-C_6)$alkyl groups; halo$(C_1-C_6)$alkyl groups; $(C_3-C_6)$cycloalkyl groups; unsubstituted phenyl groups; substituted phenyl groups having one or more substituents which may be the same or different and are selected from the group consisting of halogen atoms, $(C_1-C_6)$alkyl groups and $(C_1-C_6)$alkoxy groups; or 5- or 6-membered heterocyclic rings containing, between adjacent carbon atoms of the carbon chain, one or more hetero atoms which may be the same or different and are selected from the group consisting of oxygen atom, sulfur atom and nitrogen atom; $R^{28}$ and $R^{29}$ being able to be taken together to represent a $(C_3-C_6)$cycloalkane ring or a 5- or 6-membered heterocyclic ring containing one or more sulfur atoms between adjacent carbon atoms of the carbon chain), or $R^6$ and $R^{27}$ being able to be taken together with the nitrogen atom to which they are bonded, to represent a 5- or 6-membered heterocyclic ring which may contain, between adjacent carbon atoms of the carbon chain, one or more hetero atoms which may be the same or different and are selected from the group consisting of oxygen atom, sulfur atom and nitrogen atom].

9. The method of claim 1, wherein $R^1$ is ① a hydrogen atom, ② a $(C_1-C_{12})$alkyl group, ③ a halo$(C_1-C_{12})$alkyl group, ④ a $(C_2-C_{12})$alkenyl group, ⑤ a halo$(C_2-C_{12})$alkenyl group, ⑥ a $(C_2-C_{12})$alkynyl group, ⑦ a halo$(C_2-C_{12})$alkynyl group, ⑧ a $(C_3-C_6)$cycloalkyl group, ⑨ an unsubstituted phenyl group, or ⑩ a substituted phenyl group having one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_1-C_6)$alkylthio groups, halo$(C_1-C_6)$alkylthio groups, $(C_2-C_6)$alkenyl groups and $(C_2-C_6)$alkynyl groups, and $R^2$ is (vi) a group represented by the formula:

$$-N(R^6)-OR^{30}$$

(wherein $R^6$ is as defined above, and $R^{30}$ is a hydrogen atom, a $(C_1-C_{12})$alkyl group, a halo$(C_1-C_{12})$alkyl group, a $(C_3-C_6)$cycloalkyl group, a $(C_2-C_{12})$alkenyl group, a $(C_2-C_{12})$alkynyl group, an unsubstituted phenyl$(C_1-C_6)$ alkyl group, or a substituted phenyl$(C_1-C_6)$alkyl group having on the ring one or more substituents which may be the same or different and are selected from the group consisting of halogen atoms, nitro group, cyano group, $(C_1-C_6)$alkyl groups, halo$(C_1-C_6)$alkyl groups, $(C_1-C_6)$alkoxy groups, halo$(C_1-C_6)$alkoxy groups, $(C_2-C_6)$alkenyl groups and $(C_2-C_6)$alkynyl groups).

10. The method of claim 1, wherein the 1,2,3-thiadiazole derivative or salt thereof is applied at a dosage of 0.1 g to 10 kg per 10 acres for protecting useful crops against the diseases.

* * * * *